United States Patent
Tripathi et al.

(10) Patent No.: US 12,349,972 B2
(45) Date of Patent: Jul. 8, 2025

(54) SURGICAL APPLICATIONS WITH INTEGRATED VISUALIZATION CAMERA AND OPTICAL COHERENCE TOMOGRAPHY

(71) Applicant: ALCON INC., Fribourg (CH)

(72) Inventors: Ashok Burton Tripathi, Santa Barbara, CA (US); George Charles Polchin, Santa Barbara, CA (US); Maximiliano Ramirez Luna, Santa Barbara, CA (US); Patrick Terry, Goleta, CA (US); Thomas Paul Riederer, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/636,470

(22) Filed: Apr. 16, 2024

(65) Prior Publication Data

US 2024/0268659 A1 Aug. 15, 2024

Related U.S. Application Data

(63) Continuation of application No. 17/108,481, filed on Dec. 1, 2020, now Pat. No. 11,986,240.

(Continued)

(51) Int. Cl.
*A61B 3/10* (2006.01)
*A61B 3/08* (2006.01)
(Continued)

(52) U.S. Cl.
CPC ............... *A61B 3/102* (2013.01); *A61B 3/08* (2013.01); *A61B 3/107* (2013.01);
(Continued)

(58) Field of Classification Search
CPC ........... A61B 3/102; A61B 3/08; A61B 3/107; A61B 3/0025; A61B 3/132;
(Continued)

(56) References Cited

U.S. PATENT DOCUMENTS 8,398,236 B2 * 3/2013 Juhasz ................... A61B 3/102
351/208
11,986,240 B2 * 5/2024 Tripathi .............. A61F 9/00834
(Continued)

*Primary Examiner* — Mohammed A Hasan
(74) *Attorney, Agent, or Firm* — Nayyer J. Siddiqi; Quinn IP Law

(57) ABSTRACT

A system for guiding an ophthalmic procedure is disclosed. The system includes a housing assembly with a head unit configured to be at least partially directed towards a target site in an eye. An optical coherence tomography (OCT) module and stereoscopic visualization camera are at least partially located in the head unit and configured to obtain a first set and a second set of volumetric data, respectively. A controller is configured to register the first set and second set of volumetric data to create a third set of registered volumetric data. The third set and second set of registered volumetric data are rendered, via a volumetric render module, to a first and second region. The first region and the second region are overlaid to obtain a shared composite view of the target site. The controller is configured to extract structural features and/or enable visualization of the target site.

19 Claims, 19 Drawing Sheets

Related U.S. Application Data

(60) Provisional application No. 62/943,965, filed on Dec. 5, 2019.

(51) Int. Cl.
  *A61B 3/107* (2006.01)
  *A61F 9/007* (2006.01)
  *A61F 9/008* (2006.01)

(52) U.S. Cl.
  CPC ...... *A61F 9/00736* (2013.01); *A61F 9/00834* (2013.01); *A61F 2009/00846* (2013.01); *A61F 2009/00851* (2013.01); *A61F 2009/00855* (2013.01)

(58) Field of Classification Search
  CPC .............. A61F 9/00736; A61F 9/00834; A61F 2009/00846; A61F 2009/00851; A61F 2009/00855
  USPC ........................................................ 351/208
  See application file for complete search history.

(56) References Cited

U.S. PATENT DOCUMENTS

| | | |
|---|---|---|
| 2002/0044258 A1 | 4/2002 | Sarver et al. |
| 2016/0106304 A1* | 4/2016 | Namati ................. A61B 90/39 600/407 |
| 2018/0303574 A1* | 10/2018 | Ramirez Luna ....... H04N 13/15 |
| 2019/0117459 A1 | 4/2019 | Berlin |
| 2021/0169324 A1* | 6/2021 | Tripathi ............... H04N 13/246 |

* cited by examiner

SURGICAL APPLICATIONS WITH INTEGRATED VISUALIZATION CAMERA AND OPTICAL COHERENCE TOMOGRAPHY

PRIORITY CLAIM

This application claims priority to, and is a continuation of, U.S. Non-Provisional application Ser. No. 17/108,481, filed on Dec. 1, 2020, which claims priority to, and benefit of, U.S. Provisional Application No. 62/943,965, filed on Dec. 5, 2019, the contents of which are hereby incorporated by reference in their entirety.

INTRODUCTION

The present disclosure relates to a system for guiding an ophthalmic procedure, the system having an integrated visualization camera and optical coherence tomography module. Various imaging modalities may be employed to assist a surgical team prior to and during ophthalmic surgery. Each of these imaging modalities brings a different set of information to the table, each presenting with a unique set of issues. For example, in a corneal transplant, attempting to view the transplant through a microscope is difficult due to the transparent/semi-transparent property of the corneal tissue. When a dye is used, the dye may not stain the tissue in a way that assists visualization; for example, the dye might emphasize edges or other defects but may not sufficiently emphasize a folded, torn or wrinkled area. In order to maximize the available information, a synthesis or melding of the respective information provided by various imaging modalities is desirable. However, it is no trivial matter to precisely represent, to a user, the captures made by multiple imaging modalities as if they represent the exact same three-dimensional object in all dimensions. It is further challenging to extract useful information from the multiple imaging modalities during an ophthalmic procedure in real-time.

SUMMARY

Disclosed herein is a system for guiding an ophthalmic procedure. The system includes a housing assembly having a head unit configured to be at least partially directed towards the target site. An optical coherence tomography (OCT) module is at least partially located in the head unit and configured to obtain a first set of volumetric data of the target site. A stereoscopic visualization camera is at least partially located in the head unit and configured to obtain a second set of volumetric data of the target site. The second set of volumetric data includes first and second (e.g. left and right) views of the target site.

The system enables improved imaging, visualization and extraction of both structural features and pathologies and for retinal, corneal, cataract and other ophthalmic surgeries. The system is movable and may be implemented as a diagnostic imaging system and/or an ophthalmic surgical system. The system results in improved patient outcomes in many fields, such as ophthalmology, by fusing various datasets related to the patient and the surgical site. The datasets may include but are not limited to: stereoscopic visualization of the surgical site; optical coherence tomography of the patient's eye in whole, or in part. The datasets may include other volumetric scanning techniques, such as ultrasound and magnetic resonance imaging and one or more refractive models of the eye, which may be generated using eye characterization techniques.

The system includes a controller in communication with the stereoscopic visualization camera and the OCT module. A volumetric render module is selectively executable by the controller and/or a camera processor integrated within the stereoscopic visualization camera. The controller has a processor and tangible, non-transitory memory on which instructions are recorded. The controller is configured to register the first set of volumetric data from the OCT module with the second set of volumetric data from the stereoscopic visualization camera to create a third set of registered volumetric data. The third set of registered volumetric data is rendered, via the volumetric render module, to a first region to obtain a two-dimensional OCT view. The second set of volumetric data from the stereoscopic visualization camera is rendered, via the volumetric render module, to a second region to obtain a live two-dimensional stereoscopic view.

The first region and the second region are overlaid to obtain a shared composite view of the target site, with the controller being configured to visualize and/or extract features of the target site from the shared composite view. In another embodiment, the system includes a visualization camera at least partially located in the head unit and configured to obtain a second set of two-dimensional image data or two-dimensional image of the target site, the two-dimensional image including first and second views of the target site. The controller is configured to register the first set of volumetric data from the OCT module with the image data from the visualization camera to create a third set of registered volumetric data. The third set of registered volumetric data is rendered to a first region to obtain a multi-dimensional OCT view, via a volumetric render module; selectively executable by the controller. The second set of two-dimensional image data from the visualization camera is rendered to a second region to obtain a live multi-dimensional view, via the volumetric render module. The first region and the second region are overlaid to obtain a shared composite view of the target site.

In one example, the controller is configured to obtain a plurality of depth scans extending through a corneal surface, with each of the plurality of depth scans defining respective starting points. A point cloud is generated or collected from the respective three-dimensional locations corresponding to the respective starting points of the plurality of depth scans. The point cloud is converted to obtain an extracted curvature. Obtaining the extracted curvature may include interpolating between the respective starting points.

The extracted curvature may be characterized by a plurality of depths. In one example, the controller is configured to visualize the shared composite view with a plurality of topographic levels. The plurality of topographic levels respectively represent the plurality of depths such that the extracted curvature may be visualized.

In another example, the ophthalmic procedure is a cataract surgery including implantation of an intraocular lens into the eye. The controller may be configured to add at least one annotation over the shared composite view on a display such that the annotation indicates a portion of the extracted curvature. The relative position of the annotation in the shared composite view may be maintained, and the extracted curvature may be used to guide alignment of the intraocular device to the eye. The first set of volumetric data is configured to be updated at a first frequency and the second set of volumetric data is configured to be updated at a second frequency. The updating of the first set of volumetric data and the second set of volumetric data may be synchronized to facilitate the alignment of the intraocular device to the eye.

In yet another example, the controller may be configured to obtain respective axial length measurements in real time repeatedly during the ophthalmic procedure by switching the OCT module between a first resolution mode and the second resolution mode.

In yet another example, the ophthalmic procedure is a corneal transplant. The controller may be configured to obtain a plurality of depth scans of the cornea. The controller is configured to identify and isolate a pathological region as being between a first one of the plurality of depth scans and a second one of the plurality of depth scans. The controller is configured to add at least one annotation over the shared composite view on a display, the annotation indicating the pathological region.

In yet another example, the ophthalmic procedure includes astigmatism correction. The controller may be configured to obtain a plurality of row scans of the cornea. The controller may be configured to extract a steep meridian and a flat meridian from the plurality of row scans, via tracking of respective maximum and respective minimum points of curvature on the cornea. The plurality of row scans may be arranged in a star pattern.

The system may include a robotic arm operatively connected to and configured to selectively move the head unit. The robotic arm is selectively operable to extend a viewing range of the OCT module in an axial direction, a first transverse direction and a second transverse direction. Registering the first set of volumetric data from the OCT module with the second set of volumetric data from the stereoscopic visualization camera may include: aligning the first and second views of the stereoscopic visualization camera respectively in rotation, translation and scale to the volumetric render module; and matching the respective perspectives of the first and second views of the stereoscopic visualization camera to the volumetric render module.

Prior to registering the first set of volumetric data with the second set of volumetric data, the controller is configured to obtain a transformation matrix connecting the respective space of the OCT module to the respective space of the volumetric render module. Prior to registering the first set of volumetric data with the second set of volumetric data, the controller may be configured to calibrate the OCT module and calibrate the stereoscopic visualization camera. Registering the first set of volumetric data with the second set of volumetric data may include finding a respective location and respective orientation of a center of projection of first and second two-dimensional visualization modules of the stereoscopic visualization camera relative to the respective location and the respective orientation of a respective data space of the OCT module.

Registering the first set of volumetric data with the second set of volumetric data may include aligning a local area of interest in the first set of volumetric data in position, orientation and size with the second set of volumetric data. The local area of interest may include at least one of a corneal limbus and a scleral vasculature.

The above features and advantages and other features and advantages of the present disclosure are readily apparent from the following detailed description of the best modes for carrying out the disclosure when taken in connection with the accompanying drawings.

DETAILED DESCRIPTION

Figure 1:
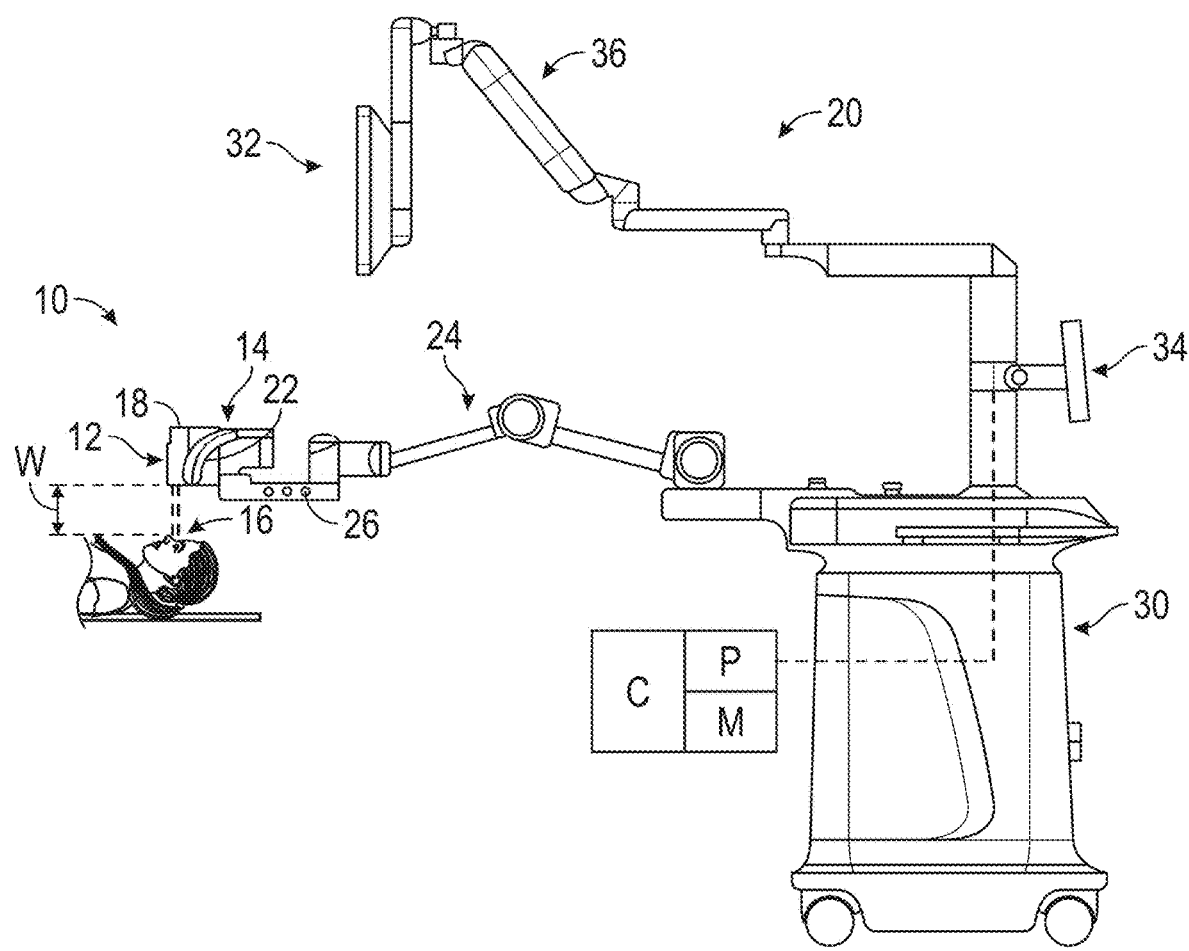
FIG. 1 is a schematic fragmentary perspective view of a system having an integrated stereoscopic visualization camera and optical coherence tomography (OCT) module.
Figure 2:
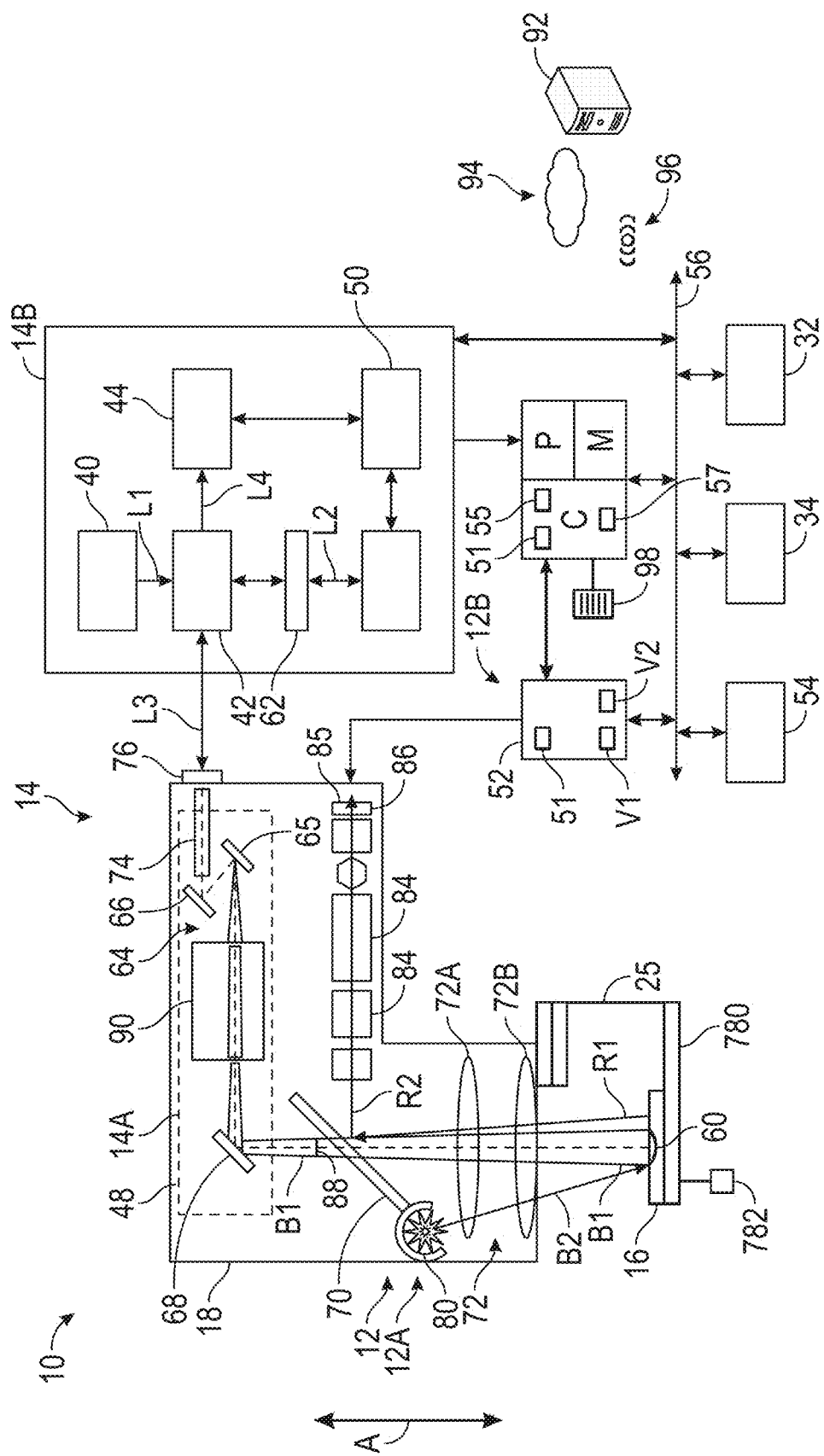
FIG. 2 is a schematic diagram of a portion of the system of FIG. 1, the system having a controller.

Referring to the drawings, wherein like reference numbers refer to like components, FIGS. 1 and 2 schematically illustrate a system 10 having a visualization camera 12, which may be a stereoscopic visualization camera 12. The visualization camera 12 may include other types of multi-dimensional imaging devices. The system 10 includes an optical coherence tomography module 14, referred to hereinafter as "OCT module" 14. The system 10 is configured to guide an ophthalmic procedure on a target site 16 in a patient's eye. Referring to FIG. 1, the stereoscopic visualization camera 12 and OCT module 14 are at least partially located in a head unit 18 of a housing assembly 20, with the head unit 18 configured to be at least partially directed towards the target site 16. As described below, the OCT module 14 is configured to obtain a first set of volumetric data of the target site 16 while the stereoscopic visualization camera 12 is configured to obtain a second set of volumetric data of the target site 16. The stereoscopic visualization camera 12 is configured to record first and second images of the target site 16, via first and second 2D visualization modules V1, V2, to generate a live two-dimensional stereoscopic view of the target site 16. By overlaying volume-rendered OCT data onto the live two-dimensional stereoscopic view of the stereoscopic visualization camera 12, the system 10 enables the detection of and response to various pathologies present in tissue.

I. System Components

Referring to FIG. 1, at least one selector 22 may be mounted on the head unit 18 for selecting specific features, such as magnification, focus and other features. The selector 22 may be employed to enable an operator to manually position the head unit 18. The system 10 may include a robotic arm 24 operatively connected to and configured to selectively move the head unit 18. For example, referring to FIG. 2, the robotic arm 24 may be selectively operable to extend a viewing range of the OCT module 14 in an axial direction A, a first transverse direction T1 and a second transverse direction T2.

Referring to FIG. 1, the head unit 18 may be mechanically coupled to the robotic arm 24 via a coupling plate 26. The coupling plate 26 may include one or more joints configured to provide further degrees of positioning and/or orientation of the head unit 18. The head unit 18 may be connected to a cart 30 having at least one display medium (which may be monitor, terminal or other form of two-dimensional visualization), such as first and second displays 32 and 34 shown in FIG. 1. The housing assembly 20 may be self-contained and movable between various locations. Returning to FIG. 1, the first display 32 may be connected to the cart 30 via a flexible mechanical arm 36 with one or more joints to enable flexible positioning. The flexible mechanical arm 36 may be configured to be sufficiently long to extend over a patient during surgery to provide relatively close viewing for a surgeon. The first and second displays 32 and 34 may include any type of display including a high-definition television, an ultra-high definition television, smart-eye-wear, projectors, one or more computer screens, laptop computers, tablet computers, and/or smartphones and may include a touchscreen.

Referring to FIGS. 1 and 2, the system 10 includes a controller C having at least one processor P and at least one memory M (or non-transitory, tangible computer readable storage medium) on which are recorded instructions for executing method 100, shown in and described below with respect to FIG. 3. The memory M can store controller-executable instruction sets, and the processor P can execute the controller-executable instruction sets stored in the memory M. Referring to FIG. 1, the controller C may be housed in the cart 30 and configured to control the robotic arm 24. The controller C may be configured to process signals for broadcasting on the first and second displays 32 and 34.

Referring now to FIG. 2, a schematic view of a portion of system 10 is shown. The head unit 18 is configured to house at least some portion of the OCT module 14 and at least some portion of the stereoscopic visualization camera 12. In one example, a first portion 14A of the OCT module 14 is housed in the head unit 18 while second portion 14B is not. Similarly, a first portion 12A of the stereoscopic visualization camera 12 is housed in the head unit 18 whereas second portion 12B is not. Referring to FIG. 2, the OCT module 14 includes a first light source 40, a beam splitter 42, a detector 44, a reference arm 46 and a sample arm 48. In one example, the detector 44 includes a spectrometer. However, it is understood that the detector 44 may include other types of receptor devices available to those skilled in the art.

The OCT module 14 and the stereoscopic visualization camera 12 may include integrated processors in communication with the controller C. For example, referring to FIG. 2, the OCT module 14 may include an OCT processor 50 and the stereoscopic visualization camera 12 may include a camera processor 52. The OCT processor 50 and camera processor 52 may be separate modules in communication with the controller C. Alternatively, the OCT processor 50 and the camera processor 52 may be embedded in the controller C. The camera processor 52 and/or the controller C are configured to selectively execute a volumetric render module 51, referred to hereinafter as "VR module," and two-dimensional stereoscopic visualization modules V1, V2. The VR module 51 may be employed with stereoscopic and non-stereoscopic data.

By integrating the OCT module 14 with the stereoscopic visualization camera 12, the system 10 enables much more immersive viewing and interaction with the image captures from the two modalities. The VR module 51 is used to display the three-dimensional data stereoscopically on a stereoscopic display. In one example, the VR module 51 may be modeled as two monoscopic volume renders separated in a horizontal direction by some intraocular distance and converging at a desired point, with some additional constraints such as the two views having the same boundaries at the focal plane of the system. For accurate fusion, the intraocular distance and convergence distance of the 2D visualization modules V1, V2 is input to the VR module 51 to achieve identical stereoscopic parameters between the two modalities.

Referring to FIG. 2, the controller C and/or the OCT processor 50 and/or the camera processor 52 may be in communication with a user interface 54 and the first and displays 32, 34, via a short-range network 56. The short-range network 56 may be a bi-directional bus implemented in various ways, such as for example, a serial communication bus in the form of a local area network. The local area network may include, but is not limited to, a Controller Area Network (CAN), a Controller Area Network with Flexible Data Rate (CAN-FD), Ethernet, blue tooth, WIFI and other forms of data connection. The short-range network 56 may be a Bluetooth™ connection, defined as being a short-range radio technology (or wireless technology) aimed at simplifying communications among Internet devices and between devices and the Internet. Bluetooth™ is an open wireless technology standard for transmitting fixed and mobile electronic device data over short distances and creates personal networks operating within the 2.4 GHz band. Other types of connections may be employed.

Referring to FIG. 2, the beam splitter 42 is configured to split incoming light L1 from the first light source 40 and send it simultaneously along a reference light path L2 into the reference arm 46, as well as along a sample light path L3 into the sample arm 48. The sample arm 48 is configured to direct at least a portion of the beam originating from the first light source 40 (split by the beam splitter 42) onto the target site 16. Referring to FIG. 2, the target site 16 is illuminated by a first beam B1. Fiber optics may be employed to transport and/or guide the first beam B1 and direct it to fall in the form of a spot scan 60 onto an appropriate region of interest in the target site 16. Other methods available to those skilled may be employed to transport and/or guide the beams within the various components of the system 10.

Referring to FIG. 2, the target site 16 onto which the spot scan 60 is directed to fall may include structures which at least partially reflect incident light arriving along first beam B1, resulting in a first reflected beam R1. The reference arm 46 is configured to reflect along the reference light path L2 at least a portion of the first light source 40 that had been split by the beam splitter 42 and sent along the reference light path L2. The reference arm 46 may include a reference arm reflecting device 62, such as a mirror or corner cube, placed at a selected distance along the reference light path L2 and configured to selectively reflect light of a specific desired wavelength. reference arm reflecting device 62 may be oriented relative to the reference light path L2 such that a relatively large portion, for example 95% or more, of the wavelengths incoming along the reference light path L2 are reflected along the reference light path L2, back towards the beam splitter 42.

Referring to FIG. 2, the beam splitter 42 is configured to optically combine the light reflected from the reference arm 46 (along reference light path L2) and the sample arm 48 and send the resulting combined beam L4 to detector 44. The respective optical lengths or travel distance of the light in the reference arm 46 and sample arm 48 are configured to match (reference light path L2 and sample path L3) such that the interference of the light reflected back from the reference arm 46 and the sample arm 48 encodes the location of multiple reflection points in the target site 16 relative to some known reference point or relative to each other. The encoding may be captured by a line-scan camera in the detector 44 and processed through spectral and Fourier analysis, via the OCT processor 50 and/or the controller C.

Referring to FIG. 2, the incoming light from the sample light path L3 is directed via a steering unit 64, downward through an optical deflecting element 70, and subsequently through a common objective lens set 72 and into the target site 16, where it strikes the target site 16 and is reflected back along the first reflected light R1. The steering unit 64 may include plurality of steering members, such as first steering member 65, second steering member 66 and third steering member 68. The incoming light from the sample light path L3 may be coupled optically with the head unit 18 via optical connector 74 and interface 76. The common objective lens set 72 may include a plurality of lenses, such as first lens 72A and second lens 72B, and other focusing devices available to those skilled in the art. A focus motor (not shown) may be employed to control magnification of the data captured by the stereoscopic visualization camera 12.

Referring to FIG. 2, the stereoscopic visualization camera 12 employs a second light source 80 located in the head unit 18 and directed through the common objective lens set 72 along a second beam B2 onto the target site 16. The first beam B1 originating in the OCT module 14 is incorporated into the head unit 18 such that it falls upon some or all of the same portion of target site 16 as the second beam B2 falls. In other words, the first beam B1 at least partially overlaps with the second beam B2 at the target site. This provides a number of technical advantages. The second portion 14B of the OCT module 14 connects optically to and from the head unit 18 via the sample light path L3. The second portion 14B may be configured to communicate with the camera processor 52 and controller C via the short-range network 56.

Referring to FIG. 2, the light arriving along the second beam B2 from the second light source 80 is reflected from the target site 16 along the first reflected light R1 back through the common objective lens set 72 to the optical deflecting element 70 which reflects the light of interest along the second reflected light R2 toward the remainder of the optical elements of the head unit 18. While in the example shown, the optical deflecting element 70 is configured to bend the light path by 90 degrees, it is understood that the angle may be varied based on the application at hand.

Referring to FIG. 2, a plurality of optical elements 84 may be employed to implement a channel (e.g. left or right) of a stereoscopic optical path and enable calibration of focus and zoom (magnification) during production as well as dynamic zoom during use. The plurality of optical elements 84 are configured to focus the second reflected light R2 onto one or more sensors, such as first sensor 85 and second sensor 86, one for each of the left view and right view making up a stereoscopic image of the target site 16. The first sensor 85 and second sensor 86 are configured to sample the light field incident upon them and may include CCD detectors or other types of detectors available to those skilled in the art.

To enable the first beam B1 to fall upon some or all of the same target site 16 on which the second beam B2 does, the optical deflecting element 70 may be coated or otherwise configured to selectively pass a given percentage of each incident wavelength of light from the first beam B1 and selectively reflect the first reflected light R1. For example, in one embodiment, the useful spectral content of the first light source 40 may reside in a Gaussian-type distribution of width from approximately 740 nanometers of wavelength to approximately 930 nanometers of wavelength, centered on a wavelength of approximately 840 nanometers. The useful spectrum of visible light for the first reflected light R1 may be about 380 or 390 nanometers to about 700 nanometers. In this case, the optical deflecting element 70 may be coated to pass wavelengths 740 to 930 nanometers as much as possible (typically 90% or more) while reflecting wavelengths 380 to 700 nanometers as much as possible (typically 90% or more).

While the second light source 80 of the stereoscopic visualization camera 12 is shown in the example in FIG. 2 as being non-coaxial to the first light source 40, it is understood that the location of the second light source 80 may be varied. For example, the position and orientation of the second light source 80 may be changed to allow co-axial lighting, such as by placing the second light source 80 behind the optical deflecting element 70 at location 88. The optical deflecting element 70 may include a bandpass filter or partial pass regime to partially pass, and hence partially reflect, light in the visible region of the spectrum.

The common objective lens set 72 are configured to provide a variable working distance W for the stereoscopic visualization camera 12. The working distance W may be referred to as the distance from a "center of projection" of an idealized camera model for the stereoscopic visualization camera 12 to a reference plane where the target site 16 is in focus. Adjusting the common objective lens set 72 changes the working distance W of the head unit 18 and thus changes the effective optical length of the sample arm 48.

Referring to FIG. 2, a working distance compensation member 90 may be employed in the sample arm 48 to offset this change in order to ensure that the reference arm 46 and the sample arm 48 have the same respective nominal optical lengths. The working distance compensation member 90 may include or more lenses, such as a liquid lens or other lens configured to complement the common objective lens set 72. For example, if adjusting the common objective lens set 72 increases the working distance by 10 millimeters, the working distance compensation member 90 located in the sample arm 48 may be controlled (e.g. via the selector 22) to similarly reduce the effective optical length of the sample arm 48.

In another embodiment, the working distance compensation member 90 may be located in the reference arm 46 and configured to match the working distance changes in the sample arm 48 by moving the reflecting surface of the reference arm 46 along the direction of travel of the reference light path L2. For example, the working distance compensation member 90 may include a micro-positioning stage to move the reflecting surface of the reference arm 46.

The OCT processor 50 and/or the controller C may be configured to control the various components of the OCT module 14, including the first light source 40, the steering unit 64 and the working distance compensation member 90. The working distance compensation member 90 may be calibrated to match the changes in path length of the sample arm 48. The controller C may be configured to execute instructions to manage overall operation of the OCT module 14. The instructions may be stored permanently in the memory M or may be uploaded dynamically. The OCT processor 50 and/or the controller C may include sub-processors and other circuitry available to those skilled in the art to communicate and control the various components of the OCT module 14.

The image stream from the stereoscopic visualization camera 12 may be sent to the camera processor 52 and/or the controller C, which may be configured prepare the image stream for viewing. For example, the controller C may combine or interleave first and second video signals from the stereoscopic visualization camera 12 to create a stereoscopic signal. The controller C may be configured to store video and/or stereoscopic video signals into a video file and stored to memory M. To view the stereoscopic display, a user may wear special glasses that work in conjunction with the first and displays 32, 34 to show the left view to the user's left eye and the right view to the user's right eye.

The controller C of FIG. 1 is specifically programmed to execute the blocks of the method 100 (as discussed in detail below with respect to FIG. 3) and may include or otherwise have access to executable programs or information downloaded from remote sources. Referring to FIG. 1, the controller C may be configured to communicate with a remote server 92 and/or a cloud unit 94, via a long-range network 96. The remote server 92 may be a private or public source of information maintained by an organization, such as for example, a research institute, a company, a university and/or a hospital. The cloud unit 94 may include one or more servers hosted on the Internet to store, manage, and process data. The long-range network 96 may be a Wireless Local Area Network (LAN) which links multiple devices using a wireless distribution method, a Wireless Metropolitan Area Networks (MAN) which connects several wireless LANs or a Wireless Wide Area Network (WAN) which covers large areas such as neighboring towns and cities. Other types of connections may be employed.

The controller C may be configured to receive and transmit wireless communication to the remote server 92 through a mobile application 98, shown in FIG. 1. The mobile application 98 may in communication with the controller C via the short-range network 56 such that it has access to the data in the controller C. In one example, the mobile application 98 is physically connected (e.g. wired) to the controller C. In another example, the mobile application 98 is embedded in the controller C. The circuitry and components of a remote server 92 and mobile application 98 ("apps") available to those skilled in the art may be employed.

II. Example Method or Implementation

Figure 3:
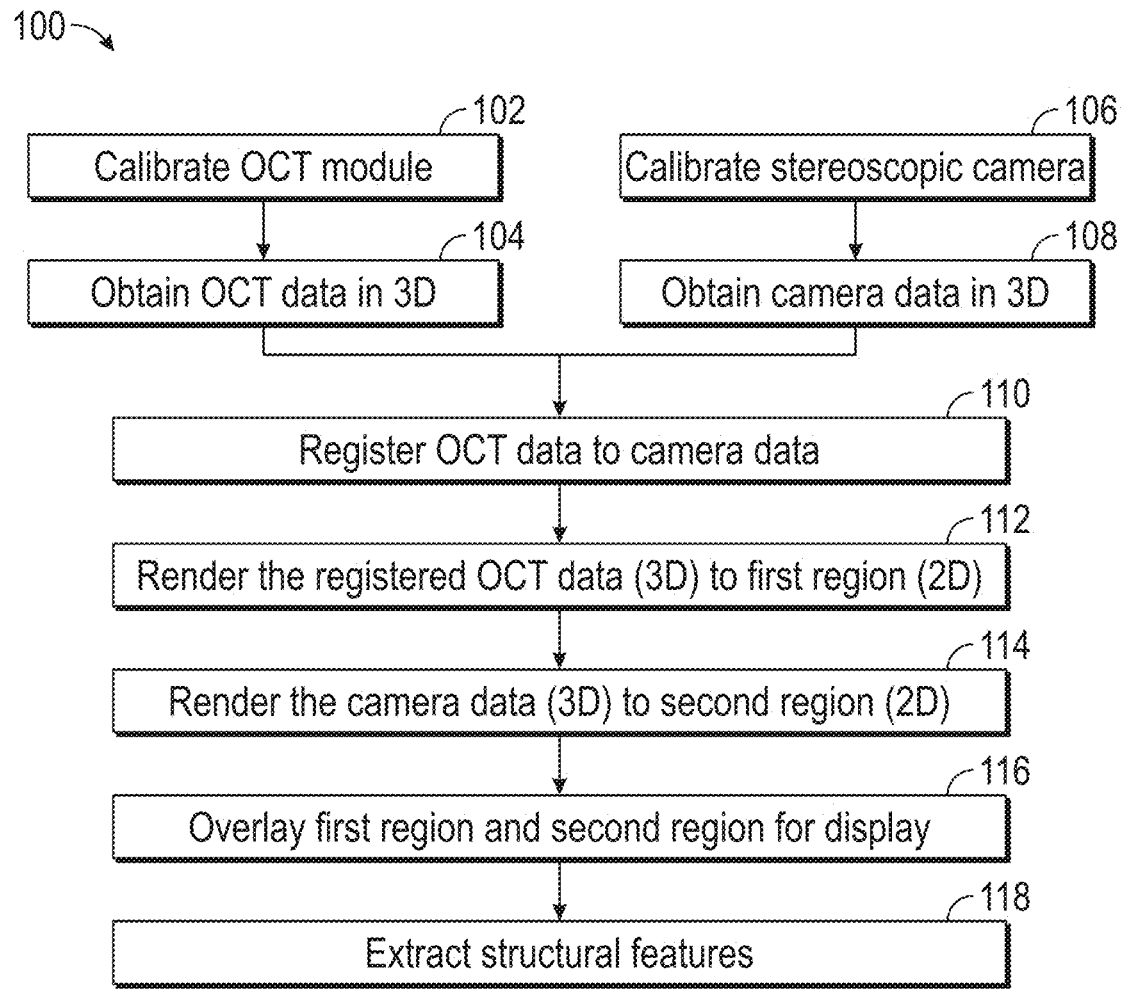
FIG. 3 is a flowchart of an example method implemented by the system of FIGS. 1 and 2 to obtain a shared composite view based on the stereoscopic visualization camera and optical coherence tomography (OCT) module.

Referring now to FIG. 3, a flow chart is shown of an example implementation or method 100 of the system 10. It is understood that the method 100 need not be applied in the specific order recited herein and some blocks may be omitted. The memory M can store controller-executable instruction sets, and the processor P can execute the controller-executable instruction sets stored in the memory M. The method 100 enables determination of a shared composite view based on the stereoscopic visualization camera 12 and optical coherence tomography (OCT) module 14.

Per blocks 102 and 104 of FIG. 3, the OCT module 14 is calibrated and a first set of volumetric data is obtained of the target site 16, via the OCT module 14. As will be described in detail below, calibrating the OCT module 14 includes calibration along an axial direction A, first transverse direction T1 and second transverse direction T2 (see FIGS. 4A-C). Per blocks 106 and 108 of FIG. 3, the stereoscopic visualization camera 12 is calibrated and a second set of volumetric data (i.e. camera data in three dimensions) from the stereoscopic visualization camera 12 is obtained.

Per block 110, the controller C is configured to register the first set of volumetric data from the OCT module with the second set of volumetric data from the stereoscopic visualization camera 12 to create a third set of registered volumetric data. Disparity mapping may be employed such that the respective output images of the stereoscopic visualization camera 12 are positioned in the same space as the respective output images of the OCT module 14. The disparity map includes the estimated pixel difference or motion between a pair of stereo images. Calibration and registration are described in detail below with respect to FIGS. 6-18.

Per block 112, the third set of registered volumetric data may be rendered, via the VR module 51 (see FIG. 1), to a first region to obtain a two-dimensional OCT view. Per block 114, the second set of volumetric data from the stereoscopic visualization camera 12 is rendered, via the VR module 51, to a second region to obtain a live two-dimensional stereoscopic view. Volume rendering refers to a three-dimensional volume reconstruction method that allows every voxel in a volumetric data to contribute to the reconstructed image. Stated differently, volume rendering is a set of techniques used to display a 2D projection of a 3D discretely sampled data set. The first and second regions may comprise a physical memory storage unit, such as a buffer, used to temporarily store data.

Figure 5:
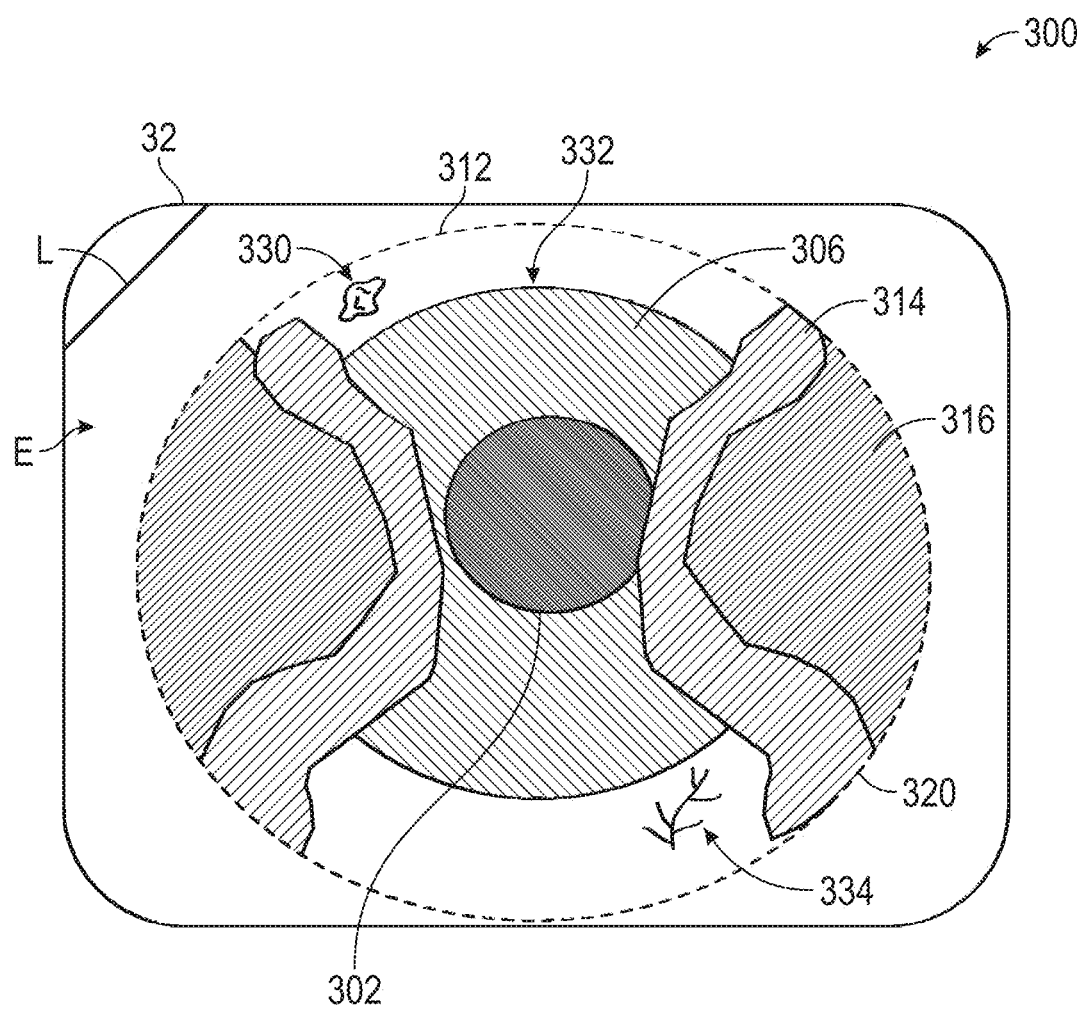
FIG. 5 is a schematic fragmentary view of an example shared composite view showing a live image of an eye overlaid with a topographic outline.

Per block 116, the first region and the second region are overlaid to obtain a shared composite view of the target site, which may be shown on at least one of the first and second displays 32, 34. An example of a shared composite view 300 of an eye E is shown in FIG. 5 and described below. Per block 118, the controller C may be configured to extract structural features from the shared composite view 300. The first set of volumetric data may be configured to be updated at a first frequency and the second set of volumetric data may be configured to be updated at a second frequency. In one example, the updating of the first set of volumetric data and the second set of volumetric data is not synchronized. Stated differently, the stereoscopic visualization camera 12 and the OCT module 14 may define a respective latency. To mitigate this, the controller C may include a first set of image buffers configured to selectively delay the display of the two-dimensional OCT view in order to match the respective latency of the stereoscopic visualization camera 12. The controller C may include a second set of image buffers configured to do the opposite, and selectively delay the display of the two-dimensional stereoscopic view to match the respective latency of the OCT module 14.

III. System Operation

Figure 4A:
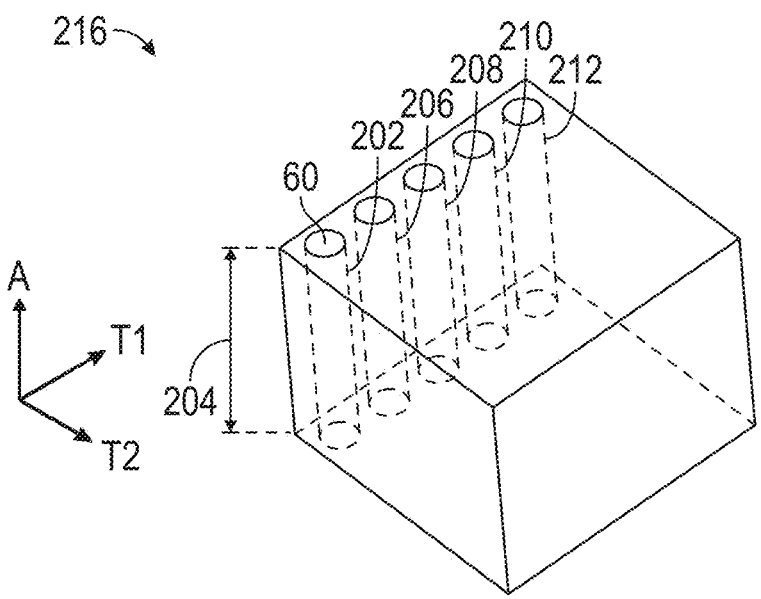
FIGS. 4A and 4B are schematic fragmentary perspective views of example scanning regions for the OCT module of FIG. 1.
Figure 4B:
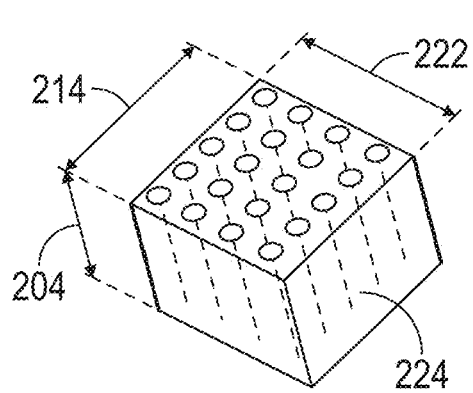
Figure 4C:
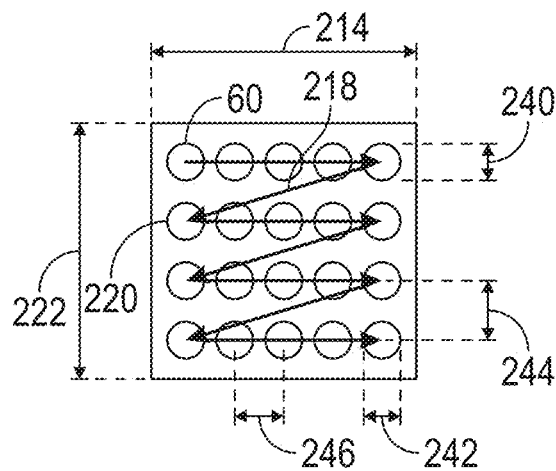
FIGS. 4C and 4D are schematic fragmentary top views of example scanning patterns for the OCT module of FIG. 1.
Figure 4D:
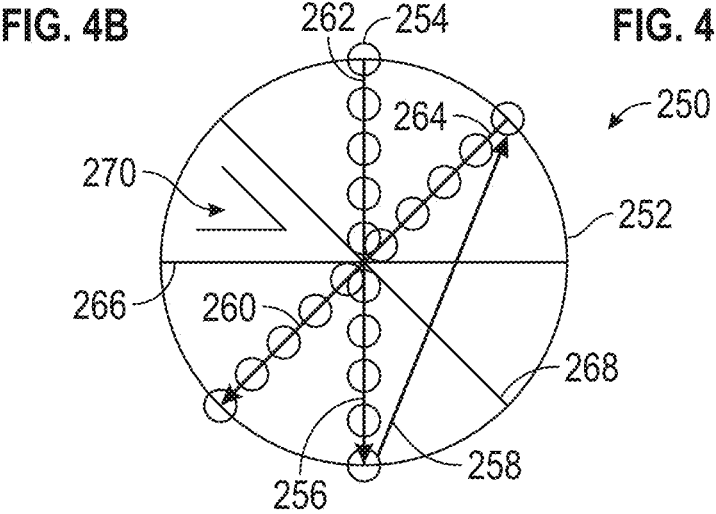

Referring now to FIGS. 4A, 4B, 4C and 4D, example scanning regions for the OCT module 14 are shown. FIGS. 4A and 4B are schematic fragmentary perspective views while FIGS. 4C and 4D are schematic fragmentary top views of example scanning patterns. Referring to FIG. 4A, a single scan directed at the spot scan 60 of the target site 16 results in a depth scan 202 of the structure of the physical sample into which the first beam B1 is directed, along the incident direction. Referring to FIG. 4A, the depth scan 202 may be referred to as an "A-scan" and is configured to scan to a detected depth 204 along an axial direction A. The axial direction A which is the travel direction of the first light source 40 in the example shown in FIG. 2.

The first beam B1 of FIG. 2 may be moved in a continual manner about the target site 16 using the steering unit 64, thereby enabling a second depth scan 206, a third depth scan 208, a fourth depth scan 210 and a fifth depth scan 212 along a first transverse scan range 214, for example. Such a line of A-scans may be referred to as a B-scan or row scan 216.

Referring to FIG. 4C, by steering the optical path appropriately along the first transverse scan range 214, then performing a "step-and-repeat" path steer along the raster pattern 218 to repeat the cycle at a starting point 220 and subsequent lines, a grid of depth scans may be traced out along the target site 16, along the first transverse scan range 214 and a second transverse scan range 222. Referring to FIGS. 4A and 4B, this results in a three-dimensional sampled volume having boundaries 224, which may have the shape of a cuboid. The steering unit 64 may be moved continually along the raster pattern 218. The boundaries 224 of the sampled volume may be determined during OCT calibration as described below.

Referring to FIG. 4A, the detected depth 204 or penetration depth for a depth scan 202 is dependent on many factors, including the spectrum of the first light source 40 at the starting point 220, the optical characteristics of the starting point 220 over the spectrum and the spectral resolution of the detector 44. Similarly, the starting point 220 may be drawn as the near extent of the dataspace of the OCT module 14; the first detected point depends on the shape and characteristics of the target site 16. Reflection points may appear as "bright" pixels in the line-scan camera data. For example, if the possible pixel values are in the range 0-255, non-reflection points might have a value of 30 or less, while bright reflection points might have a value of 150 or greater. For example, with materials such as human skin or the human eye, which are transparent or semi-transparent at the wavelengths contained in the first beam B1, the depth scan 202 may penetrate some millimeters into the material.

The movement of the first beam B1 by the steering unit 64 along with the processing of each A-scan (e.g. second depth scan 206, a third depth scan 208, a fourth depth scan 210 and a fifth depth scan 212) may be synchronized with the rest of the system 10 by the controller C and/or the OCT processor 50, such that the downstream processes may reassemble the scans in the same order and relative location during the reconstruction process. The absolute location may be determined via the calibration and registration methods described below.

In one embodiment, the steering unit 64 includes a multi-axis galvanometer or a set (for example, a pair) of single-axis galvanometers. A single-axis galvanometer is a small lightweight mirror that can rock back and forth on an axis under electrical control, thereby enabling changing the reflection direction of the path of light reflected in the mirror, but only about one axis. This enables B-scans in one transverse direction. A multi-axis galvanometer may be considered to be two single-axis galvanometers taken together. One steers the light along the B-scan direction in one transverse direction while the other steers the light along the B-scan direction in the other transverse direction. In other embodiments the steering device may be implemented as a digital micro-mirror which is typically a smaller and more lightweight version of a galvanometer but manufactured using silicon computer chip production processes. When the steering unit 64 operates using continuous movement, some blurring may occur of the data obtained by the OCT module 14 due to movement of the steering unit 64 occurring during sampling. This may be mitigated by including using stepper-motor-driven mirrors instead of galvanometers in the steering unit 64. The steering unit 64 may be selected based on the application at hand and the speed, weight, resolution, accuracy and repeatability desired.

Resolving Power and Depth of the OCT Module

The sampling resolution of the system 10 is a function of the resolution in the axial direction A (the direction of the A-scan), the diameter of a single A-scan and the separation of adjacent A-scans in each of the two remaining directions, the first transverse direction T1 and the second transverse direction T2. In one example, two different axial resolutions are possible: a first axial resolution for "high-depth, lower resolution" mode and a second axial resolution for "low-depth, higher resolution" mode. In one example, the first and second axial resolutions are approximately 20 micrometers (20 µm) and 2 micrometers (2 µm), respectively. The different axial resolutions may be implemented in this embodiment using two different light sources: a higher bandwidth light source for "low-depth, higher resolution" and a lower bandwidth light source for "high-depth, lower resolution". For optimal performance each respective light source may be mated with its own detector/spectrometer to best take advantage of the resultant bandwidth. Switching between the light source/spectrometer pairings may be achieved using an optical switch (not shown).

Referring to FIG. 4C, the diameter of the spot scan 60 may be represented by a first set of dimensions 240 and 242 and are related to factors such as the structure of the first light source 40 and the subsequent optical path encountered by the first beam B1. In one example, the first set of dimensions 240 and 242 are equal and in the range of approximately 15 µm to 80 µm. In other examples, first set of dimensions 240 and 242 are not equal. Referring to FIG. 4C, the separation of adjacent ones of the A-scans or depth scans 202 may be represented by a second set of dimensions 244 and 246, which may be equal and in the range of approximately 15 µm to 80 µm. The separation is related to factors such as the optical distance from the steering unit 64 to the target site 16 and the resolution of the steering unit 64.

As noted above, the steering unit 64 may include plurality of steering members, such as first steering member 65, second steering member 66 and third steering member 68. The resolution of the steering members affects the separation. The span of the first and second transverse scan ranges 214, 216 are related to the properties of the steering unit 64. Each of the values of the resolution in the axial direction A and the first and second transverse directions T1, T2, the axial span or detected depth 204, and the spans of the first and second transverse scan range 214 and 222 may be respectively determined during an OCT calibration process as described below.

Other Scan Patterns

Referring to FIG. 4D, other scan patterns are possible by changing the relative timing of the steering unit 64. For example, a radial scan pattern 250 may be implemented wherein a circular region 252 is sampled starting for example at scan start point 254, proceeding along radial path 256, performing a "step" along path 258 and "repeat" of (or in other embodiments, continuous travel along) the sample path 260. A simplified, faster version of this scan may include a "two B-scan" process with a single pair of scans oriented perpendicular to each other in transverse directions, which enables faster determination of movements of the target site 16 up to a speed such that the movement can be detected in these limited scans.

Referring to FIG. 4D, the radial scan pattern 250 may be employed to obtain a plurality of radial B-scans along paths 260, 262, 264, 266 and 268, and sample a cylindrical-type volume. Such a sampling pattern is advantageous, for example, when working with the surfaces of the human eye where it may be desirable to measure two-dimensional curvatures of various surfaces. The curvature is seen to lie along the sample lines, especially if the center of the sample volume is aligned with the center of curvature of the surface, as is achieved approximately using the raster pattern 218 and extracting the mean highest point, either directly from samples or using curve fitting among several-to-many samples. Referring to FIG. 4C, further improvements for such a radial scan pattern 250 include filling the cylindrical sample space by adding A-scans along connected line segments 270, which include at least two connected line segments separated by an angle.

Referring to FIG. 5, an example of a shared composite view 300 of an eye E is shown on the first display 32 (or second display 34 of FIG. 1). Also shown in FIG. 5 are the pupil 302 and iris 306 of the eye E. The front and rear surfaces of the eye E captured by the OCT module 14 may be separately extracted, and a respective topographic map generated for each such surface and overlaid with the view from the 2D visualization modules V1, V2 of the stereoscopic visualization camera 12, for example, using different patterns to represent relative depth. Referring to FIG. 5, a live stereoscopic image L of the eye E is overlaid with a topographic outline 312. The topographic outline 312 may be represented by a plurality of topographic levels, such as a first topographic level 314 and a second topographic level 316. The number of possible topographic levels is related to the axial resolution of the OCT module 14. The controller C may be configured to add at least one annotation 320 (dashed circle in FIG. 5) showing a boundary of the two-dimensional OCT view over the shared composite view 300. A second annotation 330 may indicate a landmark of the eye E. The controller C may be configured to maintain the relative position of the second annotation 330 on the first display 32 relative to other features of the eye E.

IV. System Calibration

The system 10 is configured to fuse information provided by two imaging modalities: the stereoscopic visualization camera 12 and the OCT module 14. The stereoscopic visualization camera 12 includes two 2D visualization modules V1, V2, for example, two cameras generally providing a left view and a right view of a stereoscopic image. To enable accurate and clinically useful fusion of image space information of the stereoscopic visualization camera 12 and the OCT module 14, the system 10 is configured to represent to the user the captures made by each of these two imaging modalities respectively as if they represent the same three-dimensional object, in all dimensions. Data from specific portions of the target site 16, from each modality, must be displayed in the same location or otherwise imply co-location. Additionally, the system 10 is configured to match the size and orientation throughout the image, and for images that represent multiple dimensions, across all dimensions (referred herein as matching perspective). Further, in embodiments comprising fused display of both stereoscopic visualization and stereoscopic OCT images, a left and a right view from each modality is required in combination, to comprise the image set. For optimal accuracy and visual comfort, the first and second views of each modality must appear to have identical stereoscopic parameters, such as respective intraocular distance, scale, perspective and orientation.

To do this, the captures made by each of these two imaging modalities respectively are converted to a common space in a calibration process and aligned where appropriate in position, orientation and size, in a registration process. Additionally, since the presentation to the user of such an image fusion typically relies on display devices such as a flat-panel display, the method of "moving to display space," for example by creating a two-dimensional representation, must result in the relevant parameters being represented in a matched way in the final representation for each imaging modality.

Each of the modalities used here capture different representations or properties of the target site 16. The stereoscopic visualization camera 12 captures data related to visible light while the OCT module 14 captures a set of intensities related to the position of structures on and inside the target site 16. For example, the nearly transparent anterior and posterior surfaces of the cornea are imaged by the OCT module 14 but are often difficult to clearly see with the stereoscopic visualization camera 12. The incoming data is arranged in each case according to the physical parameters of position, orientation and size of the scene objects, with the two modalities sharing these physical parameters. Use of the datasets concurrently is done by converting them to a common base dimension (such as millimeters), and registering their images by aligning them in position, orientation and scale relative to each other and/or to a known reference point. In other words, the respective image space representations of a given scene or portion of a scene will appear to be the same size, in the same orientation, at the same position, to within some tolerance.

Calibrating the OCT Module

Calibrating the OCT module 14 includes axial calibration and transverse calibration. Additionally, compensation must be made for the index of refraction of materials that the first beam B1 passes through in the target site 16. Environmental variation may be compensated for by performing the calibrations in various environmental conditions and interpolating and extrapolating the results to the current conditions. For example, the axial calibration may be performed at multiple temperatures across the expected operating range of the head unit 18 and the results as a function of temperature are fitted to a calibration curve of various complexity. Then the operating temperature of the components of the head unit 18 may be measured at the time of a surgery and the calibration curve may be used to determine the actual axial calibration for the current surgery.

Axial Calibration of the OCT Module

Figure 6A:
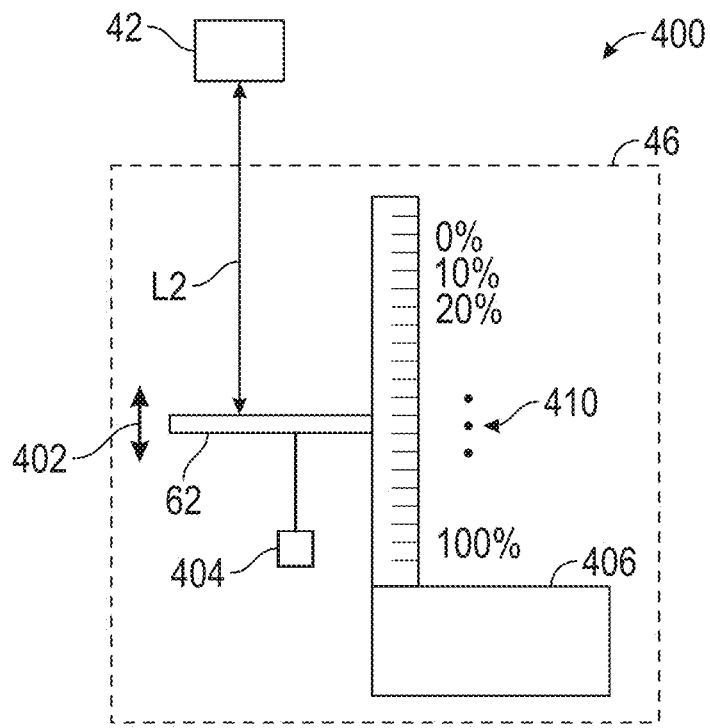
FIG. 6A is schematic illustration of an axial calibration set-up for the OCT module of FIG. 1.

Axial calibration is calibration of the distances along the first beam B1 (see FIG. 2) such that pixels in the OCT data along the depth direction or axial direction A are converted to physical units e.g. millimeters (one-thousands of a meter) or micrometers (one-thousandths of a millimeter). FIG. 6A is schematic illustration of an axial calibration set-up 400 at the reference arm 46 of the OCT module 14. FIG. 6A shows the beam splitter 42 and the reference arm reflecting device 62. The reference arm reflecting device 62 may be a flat first-surface mirror. In other embodiments, the reference arm reflecting device 62 may be a corner cube or other optical structure capable of reflecting a beam along a controlled direction with minimal loss. Referring to FIG. 6A, the axial calibration set-up 400 includes a calibrated linear motion mechanism or linear actuator 404 having a control and readout module 406 in the reference arm 46.

Figure 6B:
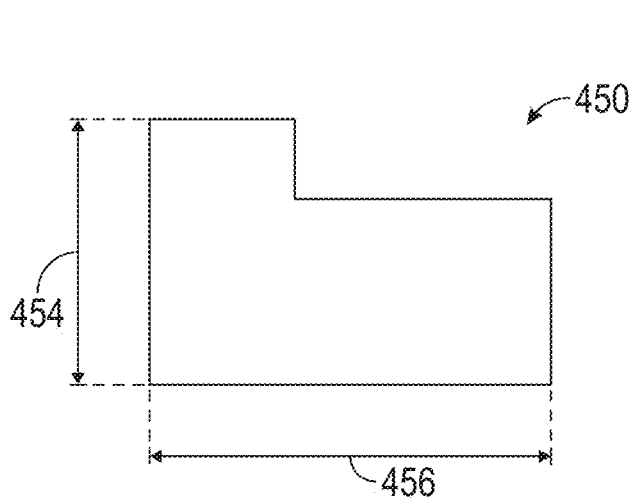
FIGS. 6B, 6C and 6D respectively illustrate a top view, a side view and a front view of an OCT axial calibration device.
Figure 6C:
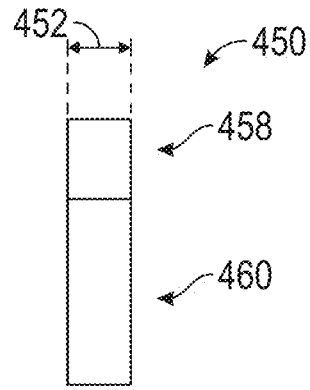
Figure 6D:
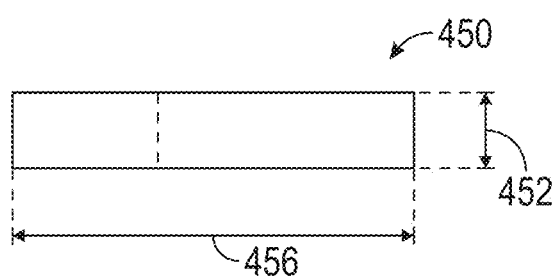

FIGS. 6B, 6C and 6D respectively illustrate a top view, a side view and a front view of a calibration device 450 for axial calibration of the OCT module 14. The calibration device 450 may be made with a nominally flat surface which is reflective to some degree. The calibration device 450 is placed in a fixed position at the scene location, i.e. the target site 16, which becomes the nominal location for all other measurements and which flat, reflective surface reflects some of the first beam B1 back toward the beam splitter 42. To facilitate relating the axial calibration information of the OCT module 14 to the focal plane F of the stereoscopic visualization camera 12, the calibration device 450 is also textured to assist with focusing the stereoscopic visualization camera 12 onto the surface. The texture is non-periodic and may be one or more of the following: inherent in the material; printed and/or affixed; and projected.

Referring to FIGS. 6B to 6D, the calibration device 450 has a first dimension 452, a second dimension 454 and a third dimension 456. The first dimension 452 or thickness dimension of the calibration device 450 is configured to be much less than the other two dimensions (e.g. 454 and 456) to avoid negative effects of axial imaging in that dimension, such as shadowing. The stereoscopic visualization camera 12 is focused onto the surface of the calibration device 450 and the value of the position of the linear actuator 404 is recorded.

Referring to FIGS. 6B to 6D, the calibration device 450 may be made into an irregular shape with a first segment 458 and a second segment 460, each with differing structural properties and differing sizes, to determine orientation. An automated algorithm available to those skilled in the art may be employed to separate the data from the first segment 458 and the second segment 460.

Figure 7A:
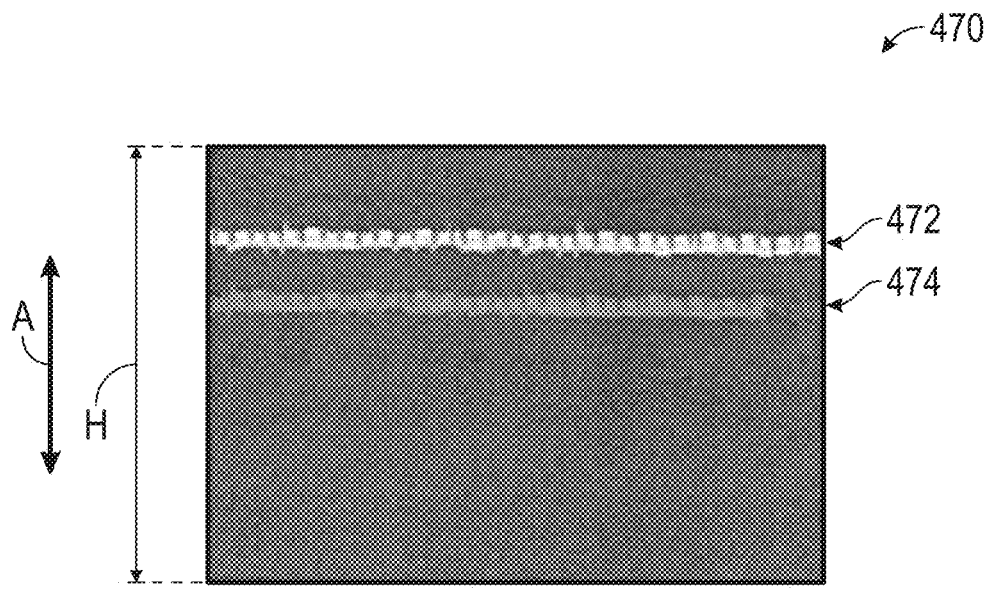
FIGS. 7A and 7B illustrate example data received from the OCT axial calibration device shown FIGS. 6B, 6C and 6D.
Figure 7B:
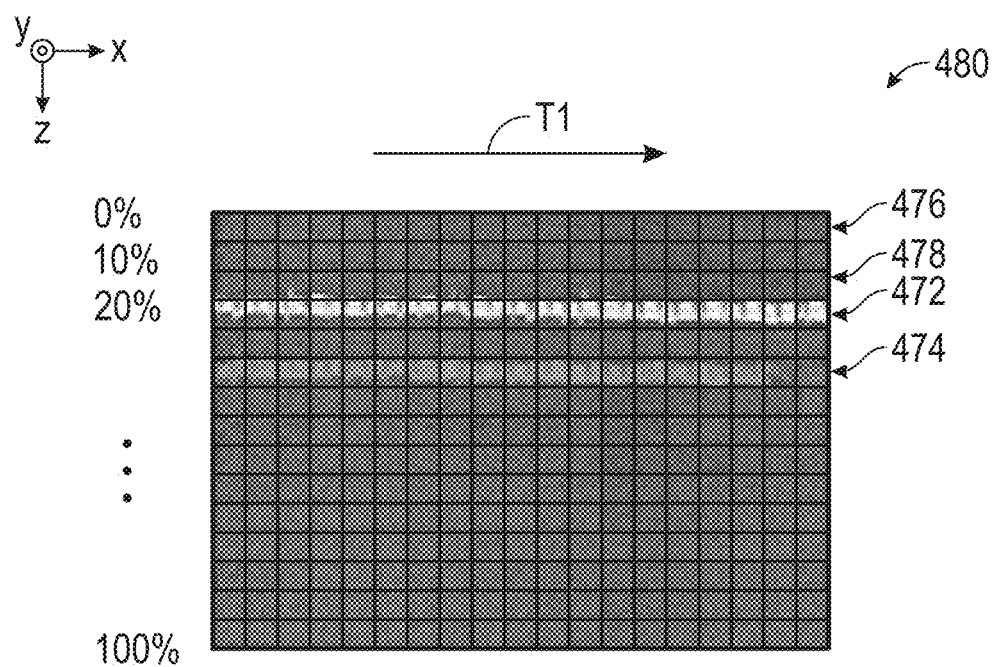

Referring now to FIG. 6A, the linear actuator 404 is first set to a starting position 410 which becomes the nominal location of the reference arm mirror 402. A first measurement is made of this setup with the surface of the calibration device 450 and reference mirror 402 as described. Referring to FIG. 7A, an output image 470 (B scan) of the surface is created and a first line 472 of "bright pixels" is observed representing a top surface of the calibration device 450. The location of the first line 472 of bright pixels along the axial direction A in the data is recorded. FIG. 7B illustrates a pixelated output image 480. Referring to FIG. 7B, in the example shown, the first line 472 is seen to occur at about 20% of the image height H (shown in FIG. 7A).

Referring to FIGS. 7A and 7B, a second line 474 of less-bright pixels is also seen and represents the rear surface of the calibration device 450. Such a line may be used as a secondary confirmation of measurement and to calibrate the effect of index of refraction of the material of the calibration device 450. Alternatively, once the axial calibration of the OCT module 14 is complete, the thickness of the calibration device 450 is measurable by counting the separation in pixels of the second line 474 from the first line 472. The vertical position in the OCT data corresponds to a focus distance of the stereoscopic visualization camera 12 represented by the setting of the linear actuator 404 at the reference arm mirror 402, and is recorded with the focus setting as a data pair such that each value may be retrieved by looking up the pair using the other value. The data pair set may be employed to match OCT data and the image data from the stereoscopic visualization camera 12 by keeping or maintaining the setting of the linear actuator 404 at its current value during operation. The linear actuator 404 with readout and control 406 is then moved an amount smaller than the expected range (e.g. detected depth 204 along the axial direction A as shown in FIG. 4A) of a given A-scan. This amount is typically one to three orders of magnitude less than the expected range. The focus of the stereoscopic visualization camera 12 is not changed. The corresponding change in "bright pixel" position in the data corresponds to the change in position of the precision linear motion mechanism for this focus setting of the stereoscopic visualization camera 12. The focus setting is included because the first beam B1 of the sample arm 48 passes through and is therefore affected by the objective lens set 72 (see FIG. 2) of the stereoscopic visualization camera 12. Thus for example if the linear actuator 404 is moved 1 millimeter and the "bright pixel" moves 100 pixels in the data then each pixel in the data is calculated to represent an axial length of 1 millimeter divided by 100 which is 10 micrometers (10 μm.) This value is added to the data pair entry for this focus setting. By continuing this process and thus moving the linear actuator 404 along its range, the axial range of the OCT module relative to the focal plane of the stereoscopic visualization camera 12 at this focus setting and actuator setting is found either directly or by extrapolation.

The OCT axial calibration data may be adjusted so that the focus setting appears at the top of the image (at 0% image height). For example, if it is desired to image only below a surface on which the stereoscopic visualization camera 12 is focused, then the location of the nominal position of the focused surface in the OCT data may be moved toward the top of the OCT data range. Controlling the axial offset of the OCT data axial range may be implemented as follows. The stereoscopic visualization camera 12 is focused on the axial calibration device 450 and the linear actuator 404 (see FIG. 6A) is adjusted until the first line 472 bright line of pixels appears at a desired first vertical location 476 (see FIG. 7B), in the data, e.g. at pixel row 0. The second line 474 appears at a second vertical location 478 (see FIG. 7B). This offset position for the reference arm 46 may optionally be used as the mounting position for the permanent reference arm mirror mount if used, for example, when the working distance compensation member 90 is implemented in the sample arm 48. The axial calibration may be performed using just a single A-scan. However, the B-scan offers the opportunity to detect the position of the axial calibration device 450 in one dimension as well as its tilt in one dimension relative to first beam B1 of the OCT module 14. Performing a complete three-dimensional volumetric sampling provides information about the other two dimensions. Additionally, such tilt and position detection assists in registration of the OCT space to the respective camera spaces of the 2D visualization modules V1, V2 of the stereoscopic visualization camera 12.

Transverse Calibration of the OCT Module

Figure 8A:
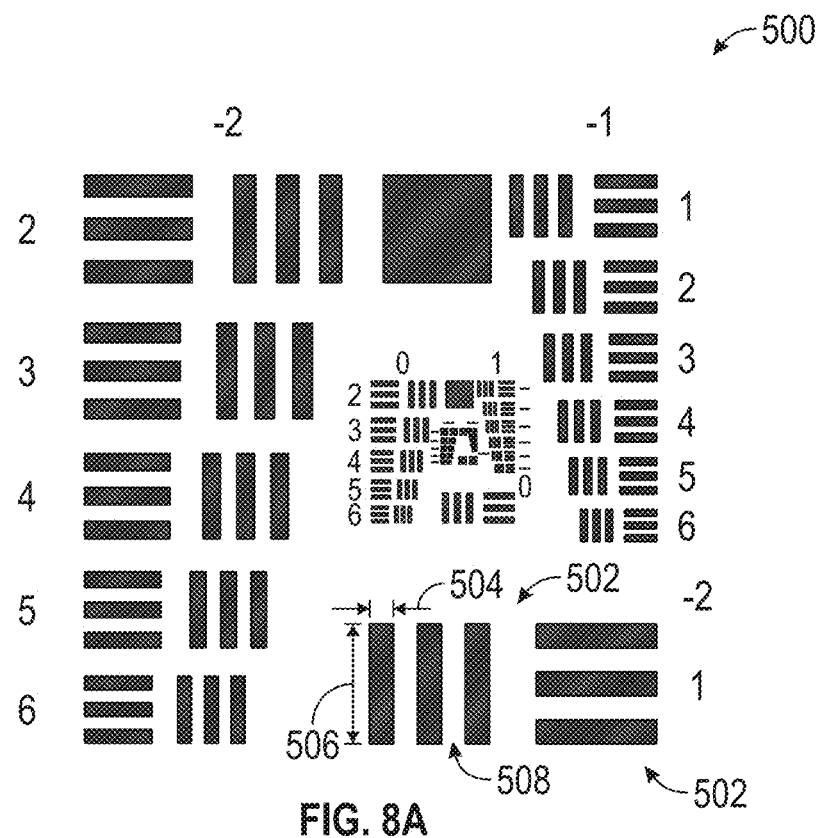
FIG. 8A is a schematic top view of a first example of a calibration target.

Calibration in each of the first and second transverse dimensions T1, T2 of the OCT scan space is achieved by viewing a patterned target with the OCT module 14. An example of a patterned target 500 is shown in FIG. 8A. The patterned target 500 has multiple bar patterns 502 with known respective widths 504, heights 506 and respective gaps 508 at multiple scales. The patterned target 500 may be printed or otherwise made to appear on a predominantly planar substrate. The thickness of the patterned target 500 is configured to be much smaller in magnitude than the other two dimensions. This reduces potential negative effects of imaging the third dimension, such as shadowing, from impacting the transverse calibrations. For example, the patterned target 500 may be printed e.g. via photolithography with chromium on a glass substrate, with a largest positive target width of 5 mm and a thickness of about 1 um or 10 um.

Figure 8B:
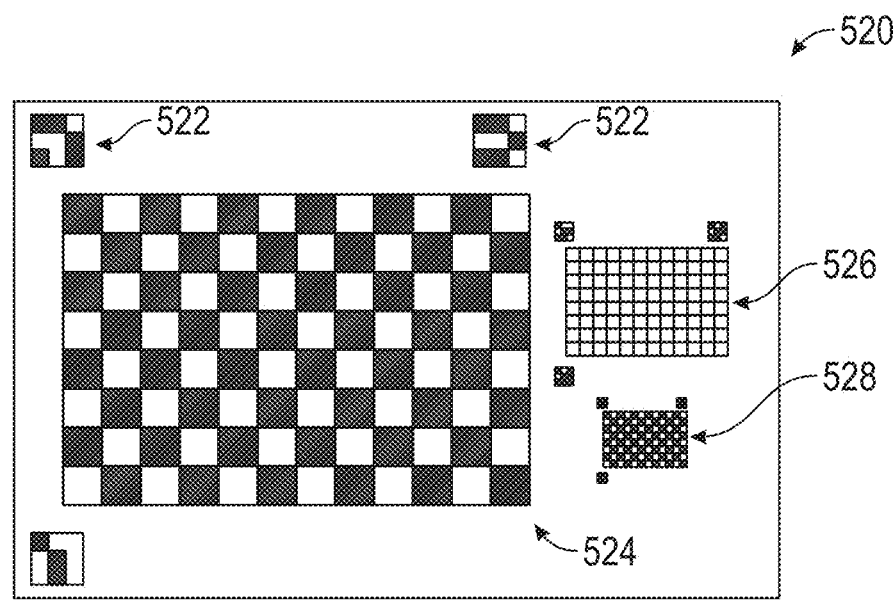
FIG. 8B is a schematic top view of a second example of a calibration target.

Referring to FIG. 8B, another example of a calibration target 520 is shown. The calibration target 520 may include multiple respective calibration sub-targets 522 having differing sizes of width, height and separation. Additionally, the calibration target 520 may include multiple varying scales 524, 526, 528. It is understood that other patterns and/or targets available to those skilled in the art may be employed.

Figure 9A:
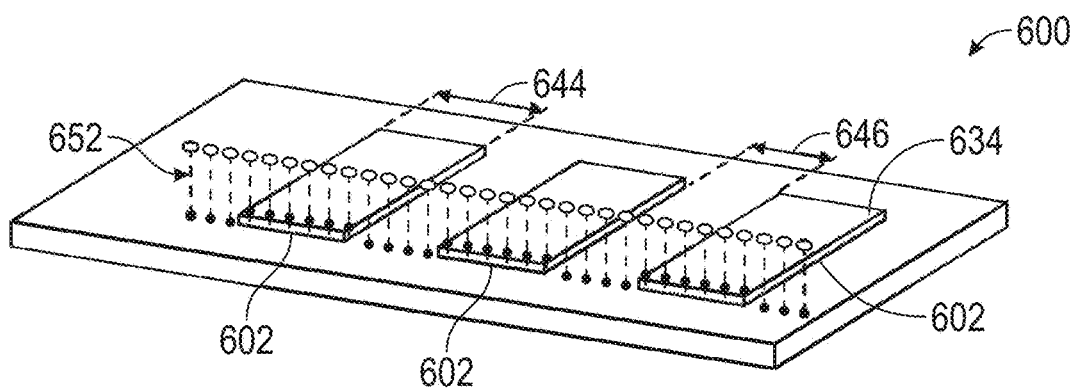
FIG. 9A is a schematic perspective view of a set-up with a plurality of calibration targets for transverse calibration of the OCT module.
Figure 9B:
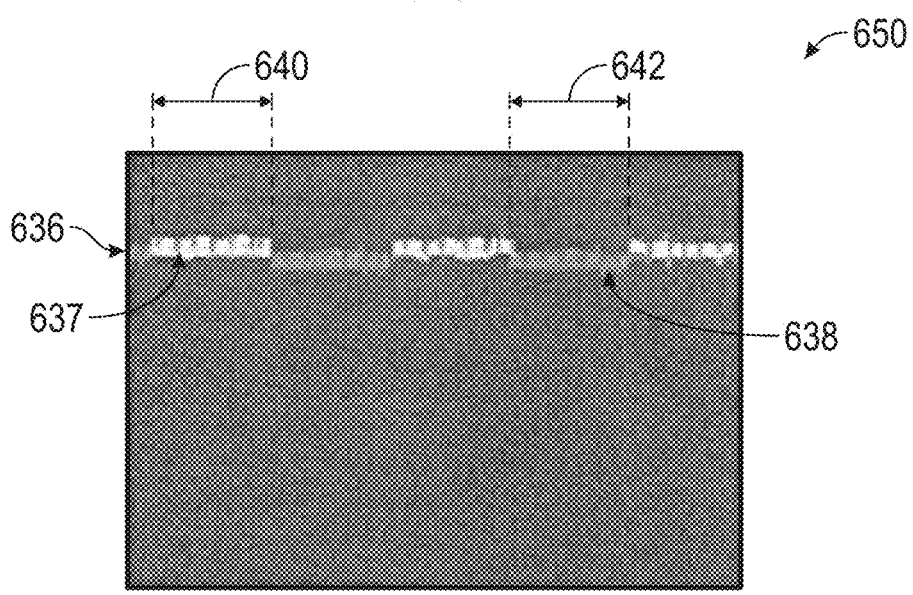
FIGS. 9B and 9C illustrate example data received from the set-up of FIG. 9A.
Figure 9C:
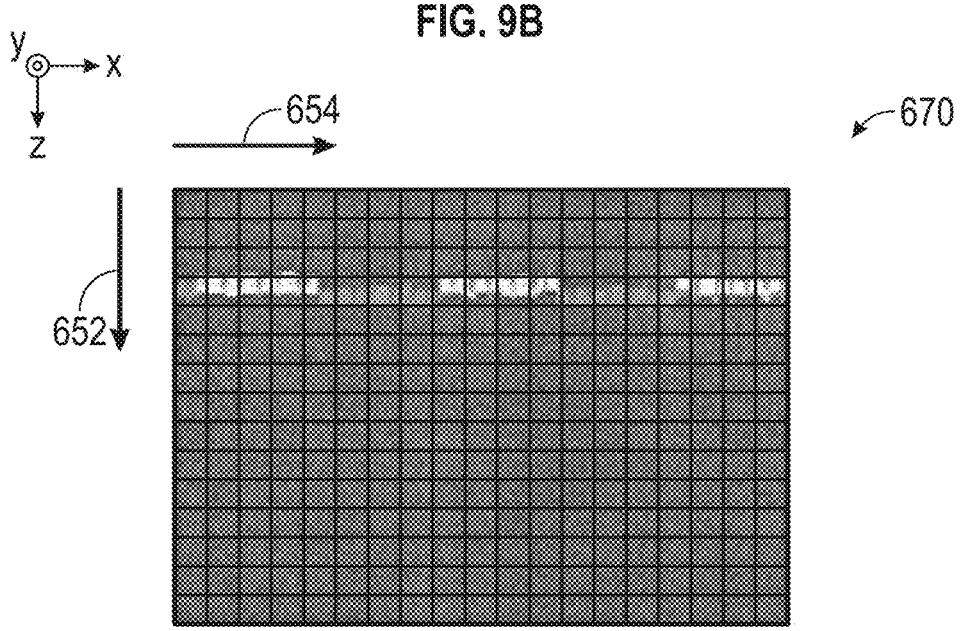

Referring now to FIG. 9A, a schematic perspective view of an apparatus 600 is shown, with a plurality of calibration devices 602 for transverse calibration of the OCT module 14. The plurality of calibration devices 602 (which may include the patterned target 500, calibration target 520 and/or other targets), is placed in the field of view and imaged by the OCT module 14. FIGS. 9B and 9C illustrate example data received from the apparatus 600 of FIG. 9A. FIGS. 9B and 9C illustrate a first output image 650 and a second output image 670, respectively. The second output image 670 shows the first output image 650 with pixel divisions. It is understood that the FIGS. are not to scale.

Referring to FIG. 9C, the A-scan direction 652 is vertical in the first and second output images 650, 670 and the B-scan direction 654 is horizontal. The predominant plane of the calibration devices 602 is assumed to be positioned orthogonally to the first beam B1. The top surface 634 (see FIG. 9A) is detected as a horizontal line 636. For further simplicity, the rear surface is not shown in these OCT images. The difference between a positive (e.g. chromium pattern line) portion 637 and a negative (e.g. empty or blank) portion 638 of the calibration devices 602 is discernible in the horizontal line 636 in the OCT data as differences in thickness and/or intensity.

From the first and second output images 650, 670, the pixel width 640 in pixels of the positive target lines may be read as approximately 4 pixels wide. Similarly, for the pixel width 642 of the negative target lines. With knowledge of the respective physical widths 644 of the calibration devices 602 and separation 646, the conversion is enabled from pixels in the transverse direction of the OCT data to physical distance in the real world. For example, if the OCT module 14 images the patterned target 500 of FIG. 8A, where the positive region is 1 mm wide and the negative region is 1 mm wide, and in the data it is measured manually or detected by the algorithm that the width in pixels of the positive portion of the patterned target 500 is 100 pixels, then the transverse resolution is calculated to be 1 mm divided by 100 pixels which is 10 um per pixel. The negative portions of the patterned target 500 may be used in some embodiments along with the positive portions to reduce the effects of measurement bias and to increase the overall number of measurement samples which increases accuracy by reducing measurement noise.

The transverse calibration method described above enables the determination of the transverse resolution of the steering unit 64 (see FIG. 2) of the OCT module 14. The change in movement control settings of the steering unit 64 between adjacent A-scans may be obtained by sub-components in the OCT processor 50 and/or controller C. Assuming the change amount is constant and the OCT beam angle does not change appreciably between A-scans, the conversion from change amount to physical distance may be obtained by dividing the change amount by the physical distance between pixels in the transverse direction of interest. Change amounts in the other transverse dimension may be found similarly. Alternatively, the change amount may be taken over many pixels (for example 10 or 100) at once and dividing it by the physical distance those many pixels are found to cover.

Fan Distortion

Referring to FIG. 2, the first beam B1 from the OCT module 14 is generally non-parallel across A-scans. This results from a narrow source and narrow beam being directed across a volume significantly wider than the source and beam and is referred to herein as fan distortion. Refinements may be made to account for fan distortion by comparing pixel patterns of a calibration device among multiple scans made with the calibration device varying in axial distance from the OCT module 14. The changes in axial distance are known from the axial calibration step, for example, by being made using a calibrated linear actuator 404 such as shown in FIG. 8A. The separation of positive and negative target regions in the OCT image data may be automated using an image processing algorithm for detecting edges available to those skilled in the art.

Transverse Offset

Similar to how axial offset is optionally adjusted to control where the "start" of the OCT data occurs in the axial dimension in physical space, the transverse scan area may be adjusted to control where the "start" or "origin" of the OCT data occurs in both of the transverse dimensions (e.g. the first and second transverse dimensions T1, T2 in FIG. 4A) in physical space. Controlling this offset is useful so that the spot scan 60 of the OCT module 14 can be moved about a given scene, as well as to set its origin in a known location either relatively or absolutely to a reference point or to the OCT module 14. For example, the upper left corner of the focal plane of one of the two 2D visualization modules V1, V2 of the stereoscopic visualization camera 12 may be used as such a reference point. The measurement of the transverse offset may be found using the above transverse calibration method and recorded for later use.

Locating OCT Space Relative to the Target Space

Figure 10A:
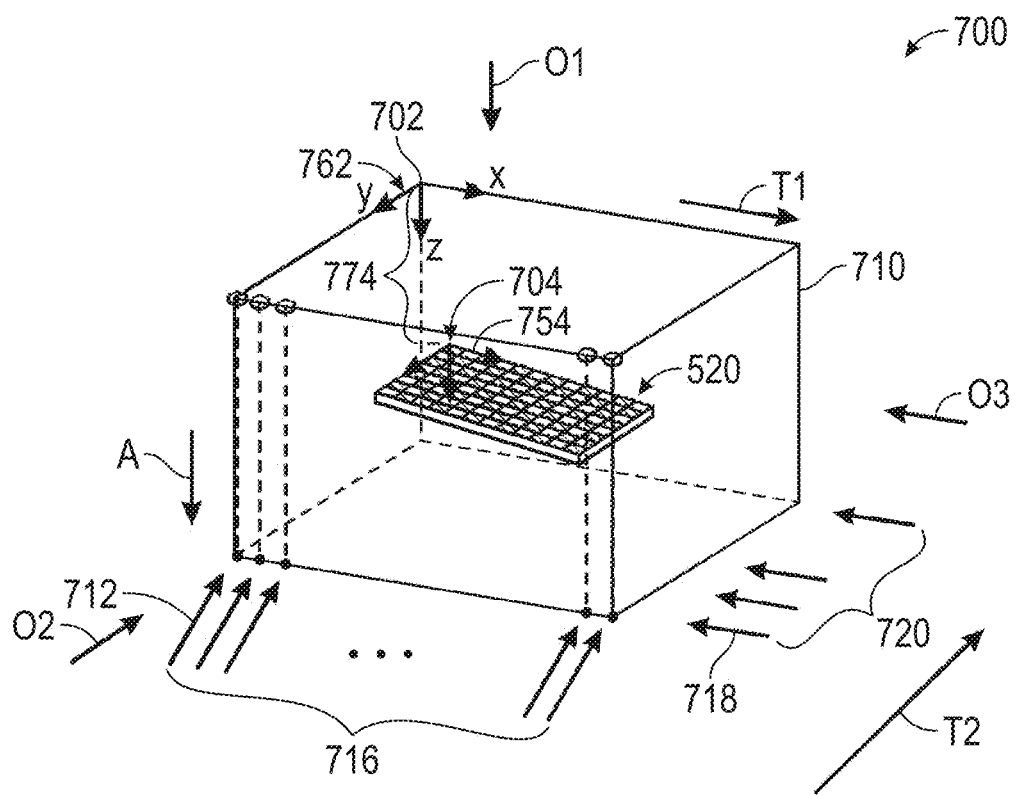
FIG. 10A is a schematic perspective view of another set-up for determining the location and orientation of respective data space of the OCT module relative to a calibration device.

FIG. 10A is a schematic perspective view of a set-up 700 for determining the location and orientation of respective data space of the OCT module relative to a calibration device defining a target space. As noted above with respect to FIG. 1, the system 10 may include a robotic arm 24 operatively connected to and configured to selectively move the head unit 18. The target space origin 702 (and orientation) of the target space may be obtained relative to the head unit 18 (housing respective portions of the stereoscopic visualization camera 12 and OCT module 14) by mounting the head unit 18 on the robotic arm 24 locating the target at a known location relative to a robot base (also known as the robot reference frame). The joint angles and link lengths of the robotic arm 24 may be obtained or are known by measurement e.g. by reading robot sensors. In another embodiment, referring to FIG. 1, a mounting stand 25 with respective mounts for the head unit 18 and the calibration target 520 may be employed, the respective mounts having known relative position and orientation.

Referring to FIG. 8B, the calibration target 520 includes multiple respective calibration sub-targets 522 having differing sizes of width, height and separation. Referring to FIG. 10A, the OCT space origin 704 relative to the target space may be found in similar ways by using a respective calibration sub-target 522 larger than the OCT space in some dimensions versus a respective calibration sub-target 522 smaller than the OCT space. In one example, a respective calibration sub-target 522 is employed that is large enough to fill or overfill the two transverse dimensions T1, T2 of the OCT space. The respective calibration sub-target 522 has features of known dimension, of known location and orientation relative to the robot reference frame and provides a means to differentiate features from each other or count them. When this respective calibration sub-target 522 is placed in the scene such that it overfills those two transverse OCT dimensions T1, T2, then the OCT space origin 704 is defined to be located at the point on the respective calibration sub-target 522, where the X=0, Y=0 pixel of the OCT data is imaged. The Z=0 location is adjusted for example to the calibration target surface using the axial offset calibration as described above. Alternatively, using a respective calibration sub-target 522 that does not fill the two transverse dimensions of the OCT space but which is planar, extrapolation 756 (see FIG. 10B) with a first group 716 of multiple A-scans and a second group 720 of multiple B-scans may be used beyond the extents of the respective calibration sub-target 522 to calculate the extents of the OCT space in the two transverse dimensions T1, T2 relative to the respective calibration sub-target 522.

Orienting the OCT Space Relative to the Target Space

Referring to FIG. 10A, a real-world space including a calibration target 520 bounded by respective OCT extents 710 is shown along with the arrangement of a single A-scan 712 along an axial direction A, as well as a first group 716 of multiple A-scans comprising a B-scan 718 in the first transverse direction T1, as well as a second group 720 of multiple B-scans in the second transverse direction T2. The OCT space origin 704 relative to the target space origin 702 may be determined by fitting a line to the first surface of the calibration target 520 in each of the three orthogonal views O1, O2 and O3 of the OCT data.

Figure 10B:
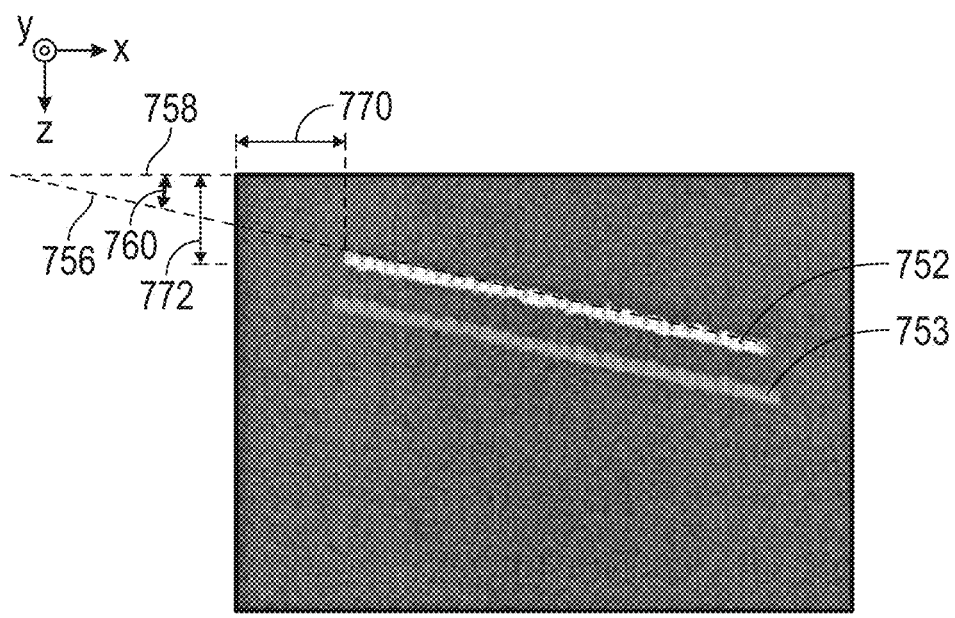
FIG. 10B is a schematic front transverse view of example data received from the set-up of FIG. 10A.

FIG. 10B is a schematic front transverse view of example data received from the set-up 700. FIG. 10B shows the upper detected edge 752 (and lower detected edge 753) of the calibration target 520 running parallel to the defined X-axis 754 of the target space. The extrapolation 756 is shown intersecting with the X-axis 758 of the OCT space. The angle 760 of this intersection is the angle that the respective X-axis of the calibration target 520 is rotated about the Y-axis 762 of the OCT space. The "inverse" of this relation is that the OCT space's Y-axis 762 is rotated about the X-axis of the calibration target 520 by the negative of the angle just found.

The relative rotations in the other dimensions may be found similarly. The origin of the calibration target 520 in the OCT space may be found similarly, with the X and Z positions being obtained as an x-axis offset 770 and a z-axis offset 772, respectively, using the front transverse view (see FIG. 10B). The y-axis offset may be obtained from a different view. The location and orientation of the OCT space relative to the target space are taken together and referred to herein as the first transformation 774 of the OCT space relative to the target space. Mathematically this information may be encoded in a transformation matrix which is read "backwards" as "the transformation from OCT space to target space." The inverse of this transformation matrix is taken to find that "the transformation from target space to OCT space" is the inverse of "the transformation from OCT space to target space." The controller C and/or the camera processor 52 and/or OCT processor 50 may include utilities, mathematical programs and other facilities available to those skilled in the art to compute this inverse as well as to multiply such matrices together.

Figure 11A:
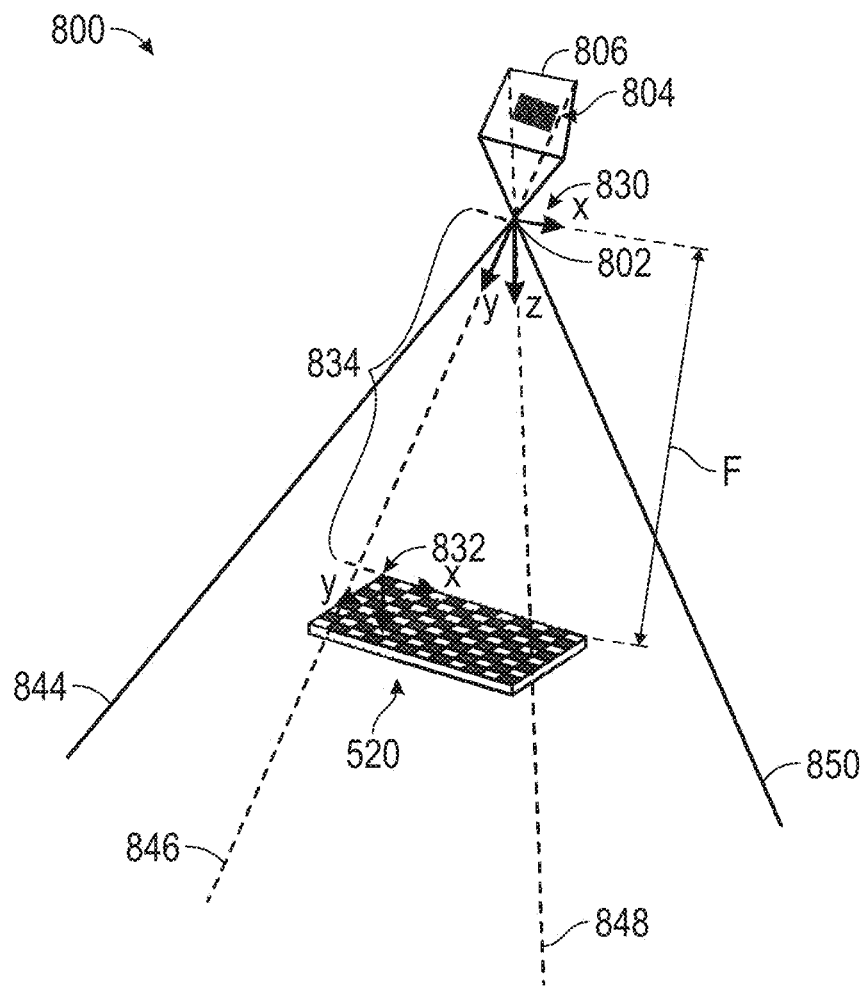
FIGS. 11A and 11B are schematic perspective views illustrating location and orientation of the calibration device (of FIG. 10A) relative to one of two monoscopic views of the stereoscopic visualization camera.
Figure 11B:
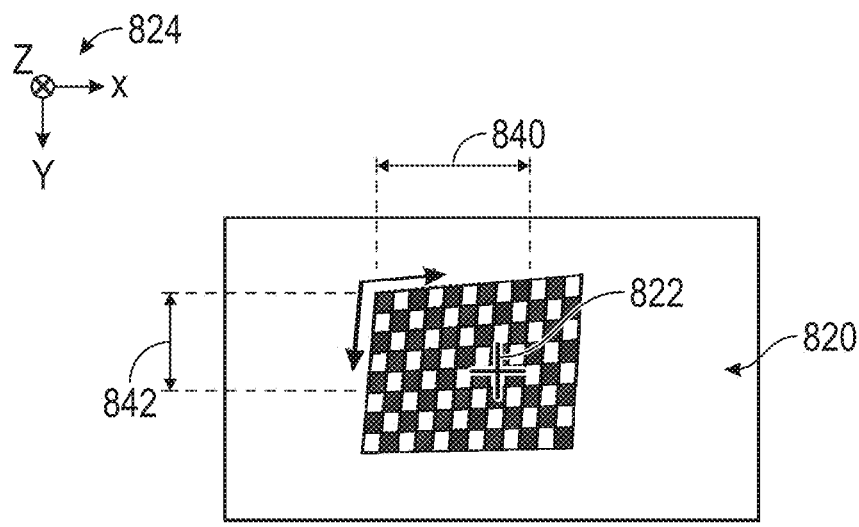

Scene Capture in 2D Visualization Modules V1, V2 of Stereoscopic Visualization Camera FIGS. 11A and 11B are schematic perspective views of a set-up 800 showing location and orientation of the calibration target 520 relative to one of two monoscopic views of the stereoscopic visualization camera 12. Viewing a given scene with a given imaging modality results in a "capture" of the scene view into the imaging modality's image space. The scene capture may be modeled in a number of ways, including with the use of a pinhole camera model. At a given zoom and working distance setting, the 2D visualization modules V1, V2 of the stereoscopic visualization camera 12 may be modeled as a simple pinhole camera wherein light from a scene (such as calibration target 520) travels through a single "pinhole" also known as the center of projection (COP) 802 and is projected such as a virtual image 804 onto an image sensor 806. This results in a two-dimensional image 820 (see FIG. 11B) of the calibration target 520 for each 2D visualization module V1, V2. For monochromatic sensors and image pixels, the image is a two-dimensional grid of pixels, the values of which are related to the light coming in from the part of the calibration target 520 which falls onto the corresponding light-sensing elements in the sensor. For color pictures, a red, green and blue filter may be employed over sensor pixels and a recombining algorithm used to combine the colors into color output pixels.

Figure 12A:
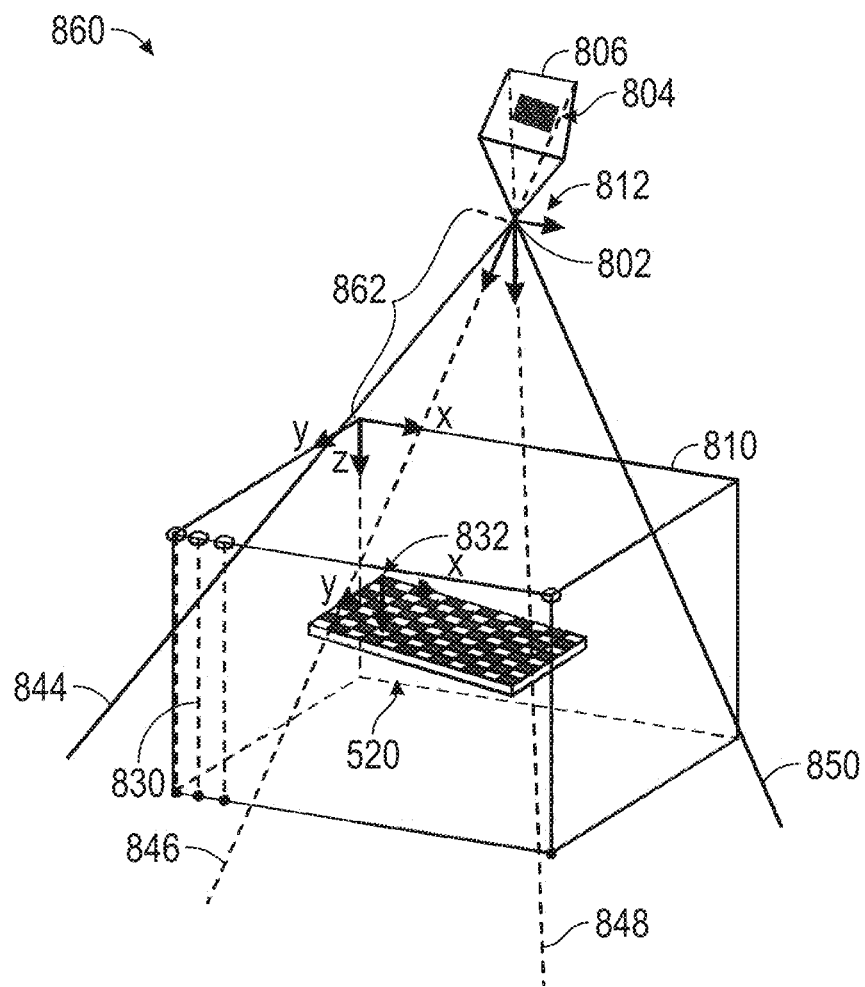
FIG. 12A is a schematic perspective view illustrating location and orientation of the respective data space of the OCT module relative to one of two monoscopic views of the stereoscopic visualization camera.
Figure 12B:
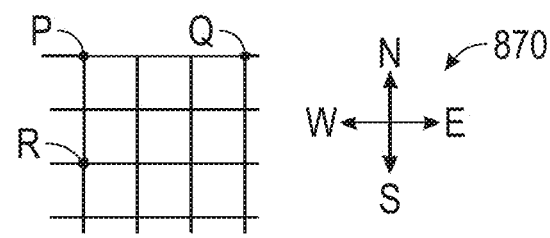
FIG. 12B is a schematic diagram illustrating the inverse relationship of a plurality of points.

Referring now to FIG. 12A, the location and orientation of the respective data space of the OCT module 14 relative to one of the two monoscopic views of the stereoscopic visualization camera 12 is shown. In the set-up 860 of FIG. 12A, the origin 812 of the coordinate system or respective space of the 2D visualization module is taken to be located at its center of projection 802. The coordinate system of an object may be referred to as the "space" of the object so that the coordinate system of the 2D visualization module may be referred to as the "COP space."

Referring to FIG. 11B, the image 820 may be considered as located in the COP space, for example, with projected axes located at position 822 and oriented as shown at axes 824. The orientation may be chosen to either obey conventions in the field of art (for example with the camera pointing down the negative Z-axis and the "right" and "up" axes of the camera being aligned along the X- and Y-axes respectively). The image may conceptually be considered located on the opposite side of the COP 802 which can flip and/or negate some axes. In some embodiments, the coordinate systems may have different origins and/or orientations and/or handedness where handedness is the relation of the X, Y, and Z axes relative to each other. For monoscopic display, the image produced may be drawn directly to the first and second displays 32, 34. Stereoscopic display entails concurrent display of (for example interleaving) the image data from each 2D visualization module, and steering the display light from one 2D visualization module to one of the user's eyes and steering the display light from the other 2D visualization module to the other of the user's eyes. Such steering may be done by using light-polarizing films of varying properties on both the display 32 and the user's glasses.

Scene Capture in the OCT Module

Capturing a single A-scan or depth scan 202 of a view of the scene or target site 16 into the image space of the OCT module results in a single line of data. This may be somewhat equivalent conceptually to a single column of pixels in an image captured by one of the 2D visualization modules V1, V2 of the stereoscopic visualization camera 12. Using the steering unit 64 to move the first beam B1 in a line, for example along axial direction A, to capture multiple A-scans results in a single B-scan which is stored in the OCT image data space as a single two-dimensional image, such as the output image 470 shown in FIG. 7A. Using the steering unit 64 to move the first beam B1 in a raster-type path such as raster pattern 218 (see FIG. 4C) results in multiple B-scans which are stored in the OCT image data space as multiple two-dimensional images such as the output image 470 of FIG. 7A. They represent a three-dimensional sampling of the three-dimensional scene space covered by the OCT space boundaries 224. The resultant data is three-dimensional when OCT data is organized as a sequence of two-dimensional B-scan images with the A-scans comprising either the vertical columns or the horizontal rows of the B-scan images, depending on configuration. Computer graphics technology may be employed with storage mechanisms, such as a three-dimensional texture as well as means to sample such data, from any three-dimensional location within the data's span. Such sampling includes algorithms to interpolate values when the sample position does not coincide with the original data position.

Displaying three-dimensional data may be achieved using the VR module 51, which results in two-dimensional images suitable for viewing on a two-dimensional display. Referring to FIG. 12A, the virtual center of projection of the VR module 51 (characterizing a virtual volume renderer camera) may be positioned virtually in the OCT space based on parameters such as the third transformation 862 (represented as a matrix) shown in FIG. 12A, determined during calibration and registration of the OCT module 14 and the stereoscopic visualization camera 12.

The VR module 51 of FIG. 2 includes a volume renderer program to generate the two 2D images from the OCT data set. In the VR module 51, rays are cast from pixel on "virtual sensor" toward data, the rays being the projected image. A stepping function is used to "grow" the ray longer and longer from the COP toward and through the OCT data and the three-dimensional texture in which the OCT data is stored is sampled at each step. When the ray is outside the OCT data, or the value of the data is zero at the ray sample point, a value of zero is considered to exist at that ray position. The final value of the pixel at the virtual image is taken as a function of the values encountered at these steps. In one embodiment such a function merely takes the maximum value encountered along the ray. Other functions accumulate the values and segment the data by thresholding the result and present different groupings as different colors for example, to enable differentiation of different tissue types in a human brain for example. Other embodiments make an estimate of the orientation of the surface at any given point in the data, which orientation is then used along with a lighting model to create the effect of a lighted surface. Resolution may be controlled by the number of pixels in the virtual image plane as well as the number of steps per ray.

Calibration of the Stereoscopic Visualization Camera

Optical calibration characterizes the intrinsic optical parameters of a given 2D visualization module having some known parameters such as pixel dimensions and other unknown parameters such as focal length and optical distortion. This enables knowledge of how a real-world structure of known dimensions will be represented in the image space of the 2D visualization module and hence also enables the converse action to within a scaling parameter: determining the dimensions of a real-world structure (to within a scaling parameter) using its image space representation in a given optically calibrated 2D visualization module. Optical calibration can also reveal extrinsic optical parameters which relate the position and orientation in the scene of a calibration object of known dimensions relative to the camera. Further, calibration of the stereoscopic visualization camera 12 determines the relationship between two 2D visualization modules V1, V2 of similar optical properties positioned and oriented near each other and enables determination of absolute values in a given set of units (e.g. millimeters) of measurements of arbitrary structures in the scene (the dimensions, positions and orientations of which do not need to be known beforehand), such as their absolute size and their position and orientation relative to some reference point on the stereoscopic visualization camera 12.

Pinhole Camera Model and Calibration

The 2D visualization modules V1, V2, at a given zoom and focus setting may be respectively modeled as a simple pinhole camera. Each of the two 2D visualization modules V1, V2 in the stereoscopic visualization camera 12 is first modeled as such separately. The relevant intrinsic parameters of such a pinhole camera are the focal length, the principal point and the optical distortion parameters. The focal length is the distance between a center of projection (aka the pinhole) and a sensor plane. The principal point is the location on the digital sensor where the center of the idealized pinhole camera lies. The distortion parameters model the optical distortion imparted on the image by the non-ideal optics of the stereoscopic visualization camera 12. Additionally, a tangential distortion parameter is modeled to attempt to describe misalignment of the camera optics path with a line emanating perpendicular to the plane of the image sensor. The extrinsic parameters obtained from the calibration include a translation and rotation, or transformation of the target relative to the stereoscopic visualization camera 12 for each calibration image captured.

Referring to FIG. 2, camera calibration may be performed at a single zoom (magnification), working distance W (and/or focal distance) setting of the stereoscopic visualization camera 12 using a calibration function 57 executable by the controller C and/or the camera processor 52. In one example, the calibration function 57 may incorporate an open source computer vision (OpenCV) function for each sensor optical path of the stereoscopic visualization camera 12. A target used during such calibration must have discernible features of known relation to each other and such features must be indexable in images of said target. That is, the location of each feature as found in an image of the target must be relatable to the actual known physical parameters of the target. An example of a calibration target 520 is shown in FIG. 8B. While calibration target 520 is shown with a checkerboard pattern, it is understood that other patterns may be employed.

Images of the calibration target 520 are taken from various viewpoints with one of the 2D visualization modules V1, V2. In some embodiments the stereoscopic visualization camera 12 is moved in three dimensions and its orientation changed relative to the calibration target 520 using the robotic arm 24 of FIG. 1. This facilitates automation of the calibration task. In other embodiments, the calibration target 520 may be moved in three dimensions and its orientation changed relative to the stereoscopic visualization camera 12 by hand or by using motorized actuators. The multiple image captures from various viewpoints of the calibration target 520 are sent into the calibration function 57 along with knowledge of its physical parameters such as width 504, height 506 and respective gaps 508 and the number of internal intersections of e.g. dark and light squares, as well as the known parameters of the 2D visualization module such as pixel dimensions. This calibration results in a focal length and principal point location for that sensor as described for the camera model. Such parameters are input into the VR module 51 to create two-dimensional images of the OCT data ready for accurate blending or "fusing" with the data from the 2D visualization modules V1, V2 of the stereoscopic visualization camera 12. This calibration also results in an estimate of optical distortion parameters.

Locating and Orienting the 2D Visualization Module Space relative to the Target Space The space of the 2D visualization module (also called "camera space") is also referred to as the "center of projection" space or COP space 830. Referring to FIG. 11A, the location (or "position" or "origin") and orientation of the target space 832 relative to the COP space 830 are taken together and referred to herein as the second transformation 834 of the target space 832 relative to the COP space 830. Besides the other parameters described, the calibration function 57 is configured to obtain an estimate of the third transformation 862 of the calibration target 520 relative to the COP space 830 for each image capture taken. Mathematically this information may be encoded in a transformation matrix.

Referring to FIG. 11A, when the calibration target 520 is oriented orthogonal to the Z-axis of the COP space 830 and the stereoscopic visualization camera 12 is focused on the calibration target 520, the plane of the calibration target 520 is a distance equal to a focal distance F away from the center of projection 802 in the negative Z direction. The origin of the calibration target 520 is shown to be translated by a first distance 840 and 842 in the X and Y directions, respectively, relative to the camera space or COP space 830. Referring to FIGS. 11A and 12A, the part of the COP space 830 that is viewable by the stereoscopic visualization camera 12 is bounded by rays 844, 846, 848 and 850. The respective OCT extents 810 are shown in FIG. 12A. The calibration target 520 is located within the rays 844, 846, 848 and 850 and nominally about the focal distance for each snapshot used in the calibration.

The calibration function 57 of FIG. 2 may include a stereoscopic function to calibrate separately each of the two 2D visualization modules V1, V2 of the stereoscopic visualization camera 12. This determines the physical relationship between the two 2D visualization modules V1, V2, such as intraocular distance and relative COP locations, and enables subsequent rectification of image pairs from the two modules into a form in which it is straightforward to determine physical dimensions in captured images when features can be found and matched in the images from the two modules. Measurement of such dimensions absolutely from the images directly is thus enabled. Determination of features' absolute position and orientation relative to some reference point on the stereoscopic visualization camera 12 is also enabled and utilizes the disparity between the locations in the first and second views of the stereoscopic visualization camera 12 of a given object or feature. Disparity is a function of how far away the object is from the stereoscopic visualization camera 12. This may be determined using a form of triangulation with the intraocular distance of the calibrated stereoscopic visualization camera 12.

By calculating the disparity of as many points in the stereoscopic image as possible (as opposed to just a single feature), a disparity map is generated which is converted to a depth map which stores locations relative to the stereoscopic visualization camera 12 for all such image points. With the OCT module calibrated and registered to the stereoscopic visualization camera 12, the image data is thus mapped to the OCT space. This enables a variety of features such as oblique viewing, which is described below with respect to FIGS. 13A, B and C. Such calibration thus provides several of the requirements of calibrating and registering the 2D visualization modules V1, V2 of the stereoscopic visualization camera 12 and the OCT module.

In one embodiment, performing camera calibration for each of the 2D visualization modules V1, V2 of the stereoscopic visualization camera 12 includes the following: field of view calibration, optical axis determination relative to some frame of reference and focus distance determination along the optical axis from some center of projection point to the focal plane, including absolute focus distance calibration. Field of view may be determined over zoom and working distance by imaging a target having known dimensions, e.g. a chessboard with known individual squares. Additionally, the corners of the squares are easily detected by image processing algorithms. Further, calibrating these parameters uses a means to alter the distance between the stereoscopic visualization camera 12 and the target by controlled amounts. Further still, for calibrating the optical axis and focus distance these amounts are measurable.

Alternative Method for Field of View Determination

The field of view at the focal plane of a real-world camera is one of the parameters needed to set up the stereoscopic volume renderer so that its output will match visually the output of the stereoscopic visualization camera 12. The field of view at the focal plane of each of the 2D visualization modules V1, V2 of the stereoscopic visualization camera 12 may be found in this alternative method as follows. The stereoscopic visualization camera 12 of the head unit 18 is presumed to have already been calibrated opto-mechanically such that the first and second optical paths are each in focus and aligned to converge vertically and horizontally at the focal plane for each zoom and working distance setting. As noted above, the calibration target 520 (see FIG. 8B) may be placed on a table 780 (see FIG. 2), which can travel nominally along the optical axis of the stereoscopic visualization camera 12 (in the z-direction here). The position of the table 780 is measured and recorded at each such measurement. The calibration target 520 may be positioned such that it nominally aligns with the camera image axes.

The stereoscopic visualization camera 12 may be set to a zoom and working distance setting, with the settings being recorded. The calibration target 520 may be brought into focus either by moving the table 780 or by changing the working distance setting of the stereoscopic visualization camera 12. A snapshot is taken of the calibration target 520 and analyzed (e.g. by counting how many squares are along the horizontal axis) to determine the horizontal field of view, the field of view being defined as "the linear dimension (i.e. width) that the stereoscopic visualization camera 12 can see at the focal plane for this zoom and working distance setting. The estimated field of view is stored in a table along with the current zoom and working distance. To avoid distortion effects which are typically worse away from the center of the image, in some embodiments only a central portion of the image is used to make the estimate and the result extrapolated to calculate the field of view dimension for the whole image. For example, if the center 25% of the image width is 10 chessboard squares wide, then the whole image width (100%) can be extrapolated to be 40 chessboard squares wide. Note that the optics of the stereoscopic visualization camera 12 in this embodiment are manufactured to tight tolerances which results in low amounts of such distortion. This means that omitting the distortion correction has little negative effect on the overall results obtained in using this form of calibration. In some embodiments the center of the calibration target 520 has different sized (e.g. smaller) component features such that when zoomed in (i.e. when at high magnification), the number of features is high enough to provide an accurate estimate of the field of view. The process may be repeated at various zoom and working distance settings across the range of both of those variables. During normal use, to get the field of view for any given zoom and working distance setting a lookup function interpolates among the closest (e.g. the closest four) values in the two-dimensional zoom/working distance space.

Method for Optical Axis and Focus Distance Calibration

The working distance W may be defined as a distance from the bottom surface of the common objective lens set 72 along the optical axis (also referred to as the view axis) to the scene or target site 16. For example, if a human viewer possessing generally pristine vision in both eyes looks at an object utilizing stereopsis, the apparent stereoscopic optical axis may be considered as a line originating from, for example, the midpoint of a line from the center of one eye to the other. Often the end of the nose is referenced for indication of the proximal end of the optical axis in scenes where the object is at a long distance. However, if the viewer closes one eye, the open eye's optical axis governs the view, and it is at a slightly different direction than that of the stereoscopic optical axis. The two human views generally focus and converge at the object. In some embodiments, the two 2D visualization modules V1, V2 of the stereoscopic visualization camera 12 may be set to focus and converge on the same point.

Focus distance may be defined as the distance from the focal plane of the stereoscopic visualization camera 12 to an origin or the center of projection along the optical axis of the stereoscopic visualization camera 12. The location and orientation of the optical axis may be determined during a calibration step in a known reference frame of the stereoscopic visualization camera 12, for example in the reference frame of the mounting stand 25 of FIG. 1. There are separate origins for each monoscopic view of the stereoscopic visualization camera 12. The distance from the focal plane of each of the 2D visualization modules V1, V2 of the stereoscopic visualization camera 12 to the respective center of projection for a pinhole camera model for each module is one of the parameters needed to set up a virtual camera (such as in the VR module 51) such that its output will match visually the output of the real-world camera. The origin is generally on the opposite side of the common objective(s) from the scene or target site 16 so focus distance is usually greater than working distance by some offset, which offset might vary with working distance and or zoom. In the stereoscopic visualization camera 12 working distance and thus focus distance changes may be implemented by moving optical elements via motors and control.

The determination of the location and orientation of the optical axis in some known reference frame of the stereoscopic visualization camera 12 as well as the position of the focal plane relative to the stereoscopic center of projection on that optical axis may be made as follows. Referring to FIG. 1, the stereoscopic visualization camera 12 and calibration target 520 are mounted to the end of the robotic arm 24 via a mounting stand 25. The link dimensions and joint configurations (e.g. sizes and angles) of the robotic arm 24 and mounting stand 25 are known by design and/or by metrology at any given time. Thus, the position and orientation of the calibration target 520 relative to the stereoscopic visualization camera 12 may be obtained relative to the mounting stand 25.

In other embodiments, the stereoscopic visualization camera 12 may be mounted to a fixed base (e.g. coupling plate 26 of FIG. 1) and the calibration target 520 mounted to a table (780 shown in FIG. 2) connected to a linear actuator 782. The position and orientation (and thus direction of travel) of the linear actuator 782 may be obtained accurately relative to the fixed base of the stereoscopic visualization camera 12. The direction of travel of the table 780 may be set by design to move nominally along the stereoscopic optical axis (the axial direction A here) and in view of the stereoscopic visualization camera 12 such that the calibration target 520 can be placed at will along the whole working distance with the stereoscopic visualization camera 12 viewing the calibration target 520 and the position read via the controls of the linear actuator 782. For highest precision, the stereoscopic visualization camera 12 may be set to maximum magnification.

Referring to FIG. 1, starting at a minimum value of the working distance W (and thus the minimum focus distance), the robotic arm 24 is configured to move the stereoscopic visualization camera 12 to align the center of the calibration target 520 with the center of both the first and second images (e.g. left and right) of the stereoscopic visualization camera 12, to within some tolerance. This ensures the calibration target 520 is centered and at the focal plane of the stereoscopic visualization camera 12. Precise orthogonality of the target site 16 and the optical axis is not required for this step. The real position and orientation of the stereoscopic visualization camera 12 relative to the center point of the calibration target 520 may be obtained from the position of the robotic arm 24 and the dimensions of the plate and are recorded. The working distance W is then changed by a portion of the full working distance range by physically moving the stereoscopic visualization camera 12 with the robotic arm 24, and then the image is re-focused, e.g. by moving a focus motor. The process of target centering and position and orientation recording is repeated, with the resultant robot move recorded. The move changes are calculated between sample points. The relative focus distances are thus determined between the points; the absolute distance from the focal plane to the center of projection at any point relies on an "absolute focus distance calibration" as described above. This is followed by another change in the working distance W and subsequent re-centering, re-focusing and reading of the robotic arm position until the entire focal length range is spanned thereby sampling this range. Since a single point on the calibration target 520 is used (the center here), the relative orientation of the calibration target 520 and stereoscopic visualization camera 12 is not needed.

An orthogonal distance regression may be performed on this series of 3D points to find the stereo optical axis with respect to some known frame on the stereoscopic visualization camera 12 for example the mounting mechanism reference frame. Projecting each of these points to this axis enables the working distance W to be calculated at each position of the focus motor that was used in the focal length range sampling. Combining these sets of information along with the absolute focus distance calibration and generating an interpolation algorithm, the position of the center of the image at the focal plane relative to the known frame on the stereoscopic visualization camera 12 is found across the entire working distance range. For endpoints of the sample range, an extrapolation algorithm is generated to reach the extents of the range not reached by the sample points.

The stereoscopic visualization camera 12 is assumed to be par-central over focus and zoom, and par-focal over zoom. If these assumptions do not hold, this procedure may have to be repeated over multiple zoom levels and interpolated. If the stereoscopic visualization camera 12 is not par-central over focus, a more complex model than the linear one may be required. These assumptions do work for the accuracy requirements on the stereoscopic visualization camera 12 currently in production.

A final step determines the "up" and "right" vectors of the stereoscopic visualization camera 12 relative to the head unit 18. In one embodiment, crosshairs may be overlaid on the visualization display, such crosshairs being aligned with a row and a column of the data such that they precisely determine the "up" and "right" vectors of the camera images. A digital overlay does this with pixel accuracy. The robotic arm 24 moves the stereoscopic visualization camera 12 such that the center point of the calibration target 520 (see FIG. 8B) is followed along the vertical crosshair and kept in focus. The movement of the robotic arm 24 is recorded such that the "up" direction of the stereoscopic visualization camera 12 is now correlated with the known robot motion. The "right" direction is determined in a similar manner.

Absolute Focus Distance Calibration

The absolute distance from the center of the focal plane to the center of projection may be estimated by placing the calibration target 520 in focus and noting the location on the calibration target 520 of the four corners of a rectangle of the display screen. Then using the table 780, the calibration target 520 is moved a known distance away from the focal plane, the camera optics are not changed (it is not refocused nor is zoom changed at all) and the new locations on the chessboard of the same four corners of a rectangle of the display screen are noted. Using the trigonometry method of similar triangles as well as additional positions of the table 780 and images, the position of the center of projection of each 2D visualization module relative to the calibration target 520 is estimated.

The location and orientation of the calibration target 520 relative to the table 780 and of the table 780 relative to the mount of the stereoscopic visualization camera 12 are known by design and by metrology. Thus, the position of the center of projection (COP) of each 2D visualization module relative to the reference frame of the stereoscopic visualization camera 12 is calculated. The choice of orientation of the "COP space" for each 2D visualization module depends on the application. In one embodiment it is chosen such that the origin is at the center of the screen with the positive X-axis running to the right and the positive Y-axis running upwards onscreen, and the 2D visualization module is looking down the negative Z-axis (so the positive Z-axis is coming out of the screen.) The whole system can be harmonized with simple mathematical adjustments via matrix multiplication(s). In another embodiment, absolute focus distance calibration is achieved by imaging a virtual shape, such as a wireframe cube, by the 2D visualization modules V1, V2 of the stereoscopic visualization camera 12 as well as the OCT module and stereoscopically rendering the output from each blended onscreen and manually altering the location of the center of projection of the volume renderer of the OCT data until the perspective of the cube matches for the two imaging modalities.

V. System Registration

Registration may be understood as the alignment in rotation, translation and scale of the two views of the stereoscopic visualization camera 12 to the respective views of the VR module 51 (embodying a virtual camera) rendering the OCT data, as well as matching the respective perspectives. While a few registration techniques are described below, it is understood that other techniques and methods may be employed. Registering the first set of volumetric data with the second set of volumetric data may include aligning a local area of interest in the first set of volumetric data in position, orientation and size with the second set of volumetric data. For example, referring to FIG. 5, the local area of interest may include a corneal limbus 332 and a scleral vasculature 334.

Registration may include finding the location and orientation of the respective centers of projection (COP) of the 2D visualization modules V1, V2 of the stereoscopic visualization camera 12 relative to the location and orientation of the OCT data space. For simplicity only one view is discussed. Finding the location and orientation of an object relative to another object is also known as finding the transformation of the coordinate system of the first object relative to the second, or vice-versa. Additionally, the coordinate system of the object is also known as the "space" of the object. A third object, which remains fixed in relative location and orientation to both objects, may be used to determine such a transform by using the inverse transform of one of the transformations. An illustration of inverse transforms is below. For example, referring to compass 870 in FIG. 12B, point Q is 4 blocks east of point P and point R is 2 blocks south of point P, and point R is 2 blocks south and 4 blocks west of point Q. The directions to get from point P to point R would be to "go 2 blocks south" and the directions to get from point Q to point R would be to "go 2 blocks south and 4 blocks west." The inverse of the directions to get from point Q to point R would be for example "go 4 blocks east and 2 blocks north" (in this example the inverse could also be "go 2 blocks north and 4 blocks east," the result is the same). Thus, directions from points P to R followed by the inverse directions from points Q to R would be "go 2 blocks south then go 4 blocks east and 2 blocks north" which gets us from points P to Q.

In this embodiment, the third object used for this maneuver is the calibration target 520 (see FIG. 8B) used elsewhere to calibrate the OCT module 14 and 2D visualization modules V1, V2. It is understood that other objects or types of devices may be used. The common physical space requirement is satisfied by the calibration steps for each of the 2D visualization modules V1, V2 and the OCT module 14 which convert their output data to real-world measurements e.g. in millimeters. The second transformation 834 (see FIG. 11A) of the calibration target 520 relative to the 2D visualization module space (the origin of which is located at the COP) may be referred to as "COP_T_TARGET" which is read "backwards" as "the transformation from target space to the center of projection space." The first transformation 774 (see FIG. 10A) of the calibration target 520 relative to the OCT space may be referred to as "OCT_T_TARGET" which is similarly read backwards as "the transformation from target space to OCT space."

To enable registration of the OCT module 14 to each of the 2D visualization modules V1, V2 of the stereoscopic visualization camera 12, the third transformation 862 (see FIG. 12A) is needed of the OCT space to the 2D visualization module space, or COP_T_OCT (or its inverse: OCT_T_COP.) COP_T_OCT may be calculated using the second transformation 834, first transformation 774 and the inverse maneuver just described:
COP_T_OCT=COP_T_TARGET*(OCT_T_TARGET).
inverse Here transformations are implemented mathematically in the controller C and/or the camera processor 52 and/or the OCT processor 50, e.g. with computer graphics using matrices, and multiple transformations are implemented by sequential multiplication of such matrices and their inverses.

Thus COP_T_OCT etc. are matrices in the actual computer code implementing these features. This equation implements registration of the two devices which when combined with proper calibration of the optical parameters of the 2D visualization module and the OCT-data-to-real-world-measurements enables accurate fusion of data from the two spaces.

Perspective Calibration

Calibration of the 2D visualization modules V1, V2 of the stereoscopic visualization camera 12 includes perspective determination which describes how objects are sized relatively in the image when the objects vary in distance to the 2D visualization modules V1, V2. This is because the three dimensions of the real world are projected onto a two-dimensional plane in a 2D visualization module. This is called "perspective projection." Objects of identical size appear in a projected image at different sizes based on how far they are from the imager's effective center of projection. Perspective calibration is the matching of this relative size scale between the stereoscopic visualization camera 12 and the OCT module 14 and is one of the critical factors in enabling accurate and realistic "fusion" of three-dimensional images from different visualization modules into a common imaging space. The OCT module 14 does not suffer from this "perspective projection" behavior because it is imaging the three-dimensional real world with three dimensions; the image data resulting from the OCT imaging process is three-dimensional and is not projected onto two dimensions.

However, representing this three-dimensional data on a two-dimensional display, such as a flat panel display, requires that it be rendered using a virtual camera such as a volume render camera characterized by the VR module 51. The perspective projection of the VR module 51 (virtual camera) needs to be set up to match that of its respective mate of the 2D visualization modules V1, V2 of the stereoscopic visualization camera 12. Note that a "3D" display is really just a 2D display which allows different 2D images ("views") to be presented to the user and therefore representing three-dimensional data requires perspective projection for each view.

The intrinsic and extrinsic parameters obtained during the camera calibration of the 2D visualization modules V1, V2 may be used to set up each respective volume render camera in the VR module 51 with a computer graphics language such that an item of known position and dimensions in the real world visualized by the calibrated stereoscopic visualization camera 12 when drawn virtually in the computer graphics pipeline portion of camera processor 52, and when positioned at an identical position and orientation relative to the calibrated stereoscopic visualization camera 12 will "match" the view of the physical object in size, shape and perspective. In a computer graphics renderer, modeling these parameters may be implemented by setting mathematical properties such as a projection matrix and a model-view matrix for controlling how a given structure is rendered onscreen including size, position, orientation and perspective.

VI. Oblique Visualization

Figure 13A:
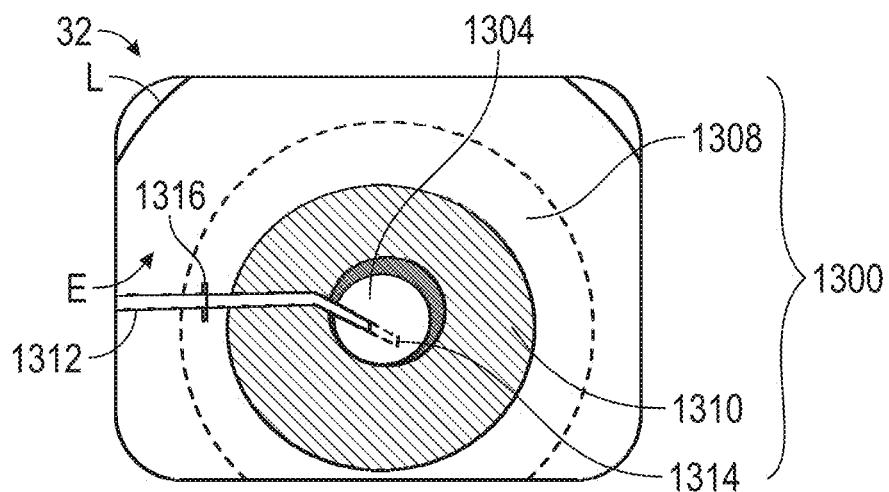
FIG. 13A is a schematic fragmentary top down view of a shared composite view of an eye.
Figure 13B:
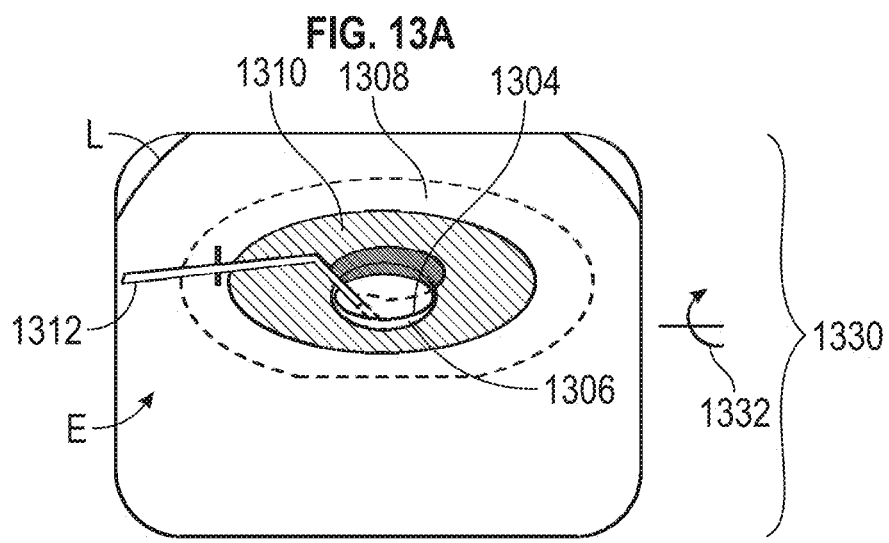
FIGS. 13B and 13C are schematic fragmentary oblique views of the eye of FIG. 13A, in accordance with a first oblique angle and a second oblique angle, respectively.
Figure 13C:
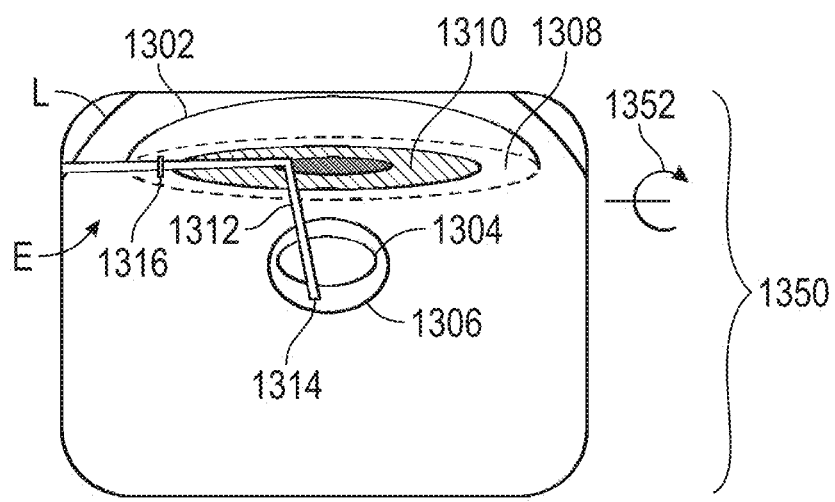

Referring to FIG. 2, the system 10 may include an oblique visualization module 55 selectively executable by the controller C to produce an off-axis view of the shared composite view such that a respective representation of the first set of volumetric data and the second set of volumetric data is viewed at a predefined oblique angle. FIGS. 13A-13C respectively illustrate a shared composite view of an eye E on a display 32 (overlaid on a live stereoscopic image L). FIG. 13A shows a top down view 1300 of the eye E with a zero-degree oblique angle. FIG. 13A illustrates an off-axis view 1330 of the eye E, in accordance with a first oblique angle 1332. FIG. 13C illustrates an off-axis view 1350 of the eye E, in accordance with a second oblique angle 1352. In the example shown, the first oblique angle is about 45 degrees and the second oblique angle is about 80 degrees.

As described above, the OCT module 14 gathers three-dimensional data from a volume in the target site 16. Referring to FIGS. 13A-C, the OCT module 14 images the nearly transparent features of the eye E, such as the cornea 1302, lens 1304 and lens capsule 1306. Execution of the oblique visualization module 55 causes the controller C to: form a virtual image, such as the virtual image 804 in FIG. 11A, based in part on the first set of volumetric data from the OCT module 14. For example, a subset of scan positions may be employed to construct the virtual image. The virtual image may be rendered, via the VR module 51, as a first pair of stereo images.

Referring to FIGS. 13A-C, the visible, generally opaque, features of the eye such as the sclera 1308 and iris 1310 are captured by the stereoscopic visualization camera 12 and disparity may be used to form the second set of volumetric data. The second set of volumetric data is rendered as a second pair of stereo images, via the VR module 51. The first pair of stereo images and the second pair of stereo images are overlaid or fused to form the off-axis view 1330 (or off-axis view 1350). Since the view of the stereoscopic visualization camera 12 is stereoscopic, calibrated and registered to the OCT view, stereoscopic visualization camera 12 is moved correctly as if it is viewed from the same arbitrary angle. The predefined oblique angle may be selectable by a user via the user interface 54.

The system 10 enables viewing and user sensing of the "depth" dimension of the eye E, which in turn, enables better control of instruments along the depth. For example, referring to FIG. 13C, the depth of a surgical tool 1312 may be most accurately imaged in the off-axis view 1350, relative to the central axis view 1300. The surgical tool 1312 may have a tip portion 1314 configured for insertion into the eye E via an incision 1316. The depth sensing via the selectable oblique angle makes it easier to keep the surgical tool 1312 from contacting or puncturing tissue, such as the anterior chamber.

In order to visualize nearly transparent features in the target site 16 (not visible to the stereoscopic visualization camera 12), portions of the OCT data may be volume-rendered as a stereo pair with nominally identical virtual camera parameters as the visible data. The rendering by the VR module 51 may be updated with every new frame of data. For example, the stereoscopic visualization camera 12 view may data updates at a frequency of nearly 60 Hz. The OCT data may update between 3 Hz and 30 Hz. These updates are independent and may or may not be synchronized. The rendering may also update to a new oblique angle when a new camera position and orientation is input by the user or other input. The output images of the stereoscopic visualization camera 12 may continue to be rendered in the same place relative to the OCT data.

VII. Surgical Applications

The system 10 may be employed in various surgical applications for a host of purposes: to enhance visualization, to evaluate the optical characteristics of the eye before, during and after surgical changes, to assist specification and placement of intraocular devices, to ease complications and to enable overall better patient outcomes. It is to be understood that the system 10 may be configured to collect data pre-operatively, intra-operatively, or peri-operatively. A number of specific applications are described below.

Extracting Structural Points and Surfaces of the Cornea

Figure 14A:
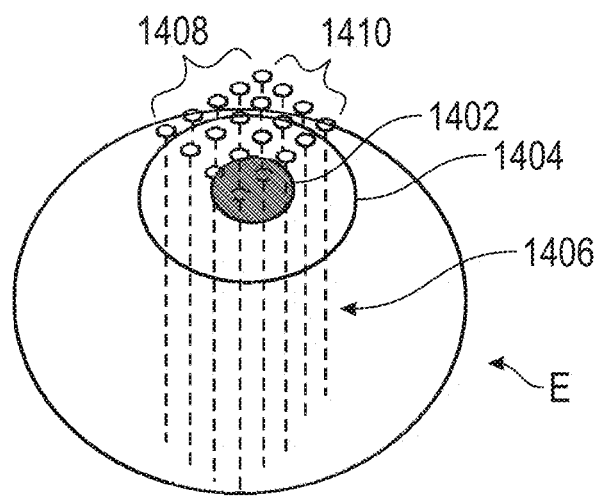
FIG. 14A is a schematic fragmentary perspective view of the eye showing a plurality of depth scans of the eye.
Figure 14B:
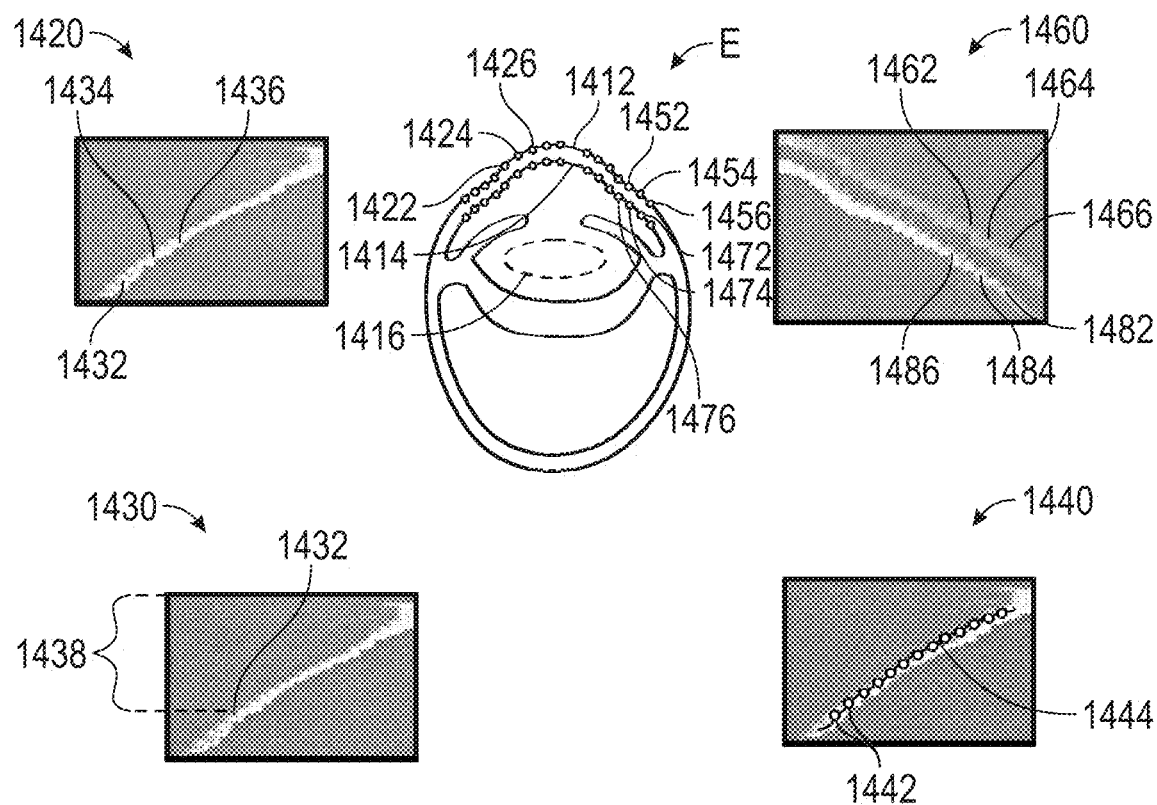
FIG. 14B shows a schematic fragmentary sectional view of the eye, along with schematic diagrams of output images obtained from the plurality of depth scans of FIG. 14A.

Referring to FIG. 14A, a schematic fragmentary perspective view of an eye E having a pupil 1402 and iris 1404 is shown. A plurality of depth scans 1406 may be employed to extract structural features of the eye E, extending across a first scan range 1408 and a second scan range 1410. Referring to FIG. 14B, a sectional view of the eye E is shown, along with output images 1420, 1430, 1460 and 1440, obtained from the plurality of depth scans 1406.

Figure 15:
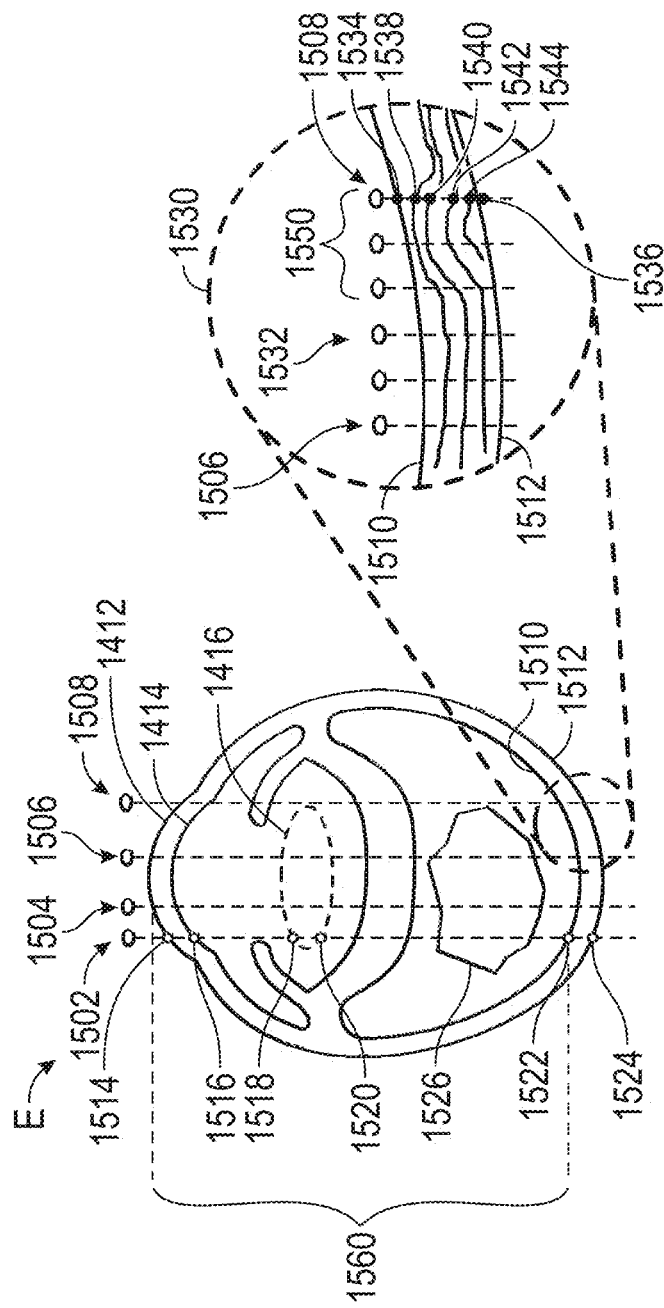
FIG. 15 is a schematic fragmentary sectional view showing the use of the system to extract a three dimensional volumetric representation of the eye.

The system 10 may be employed to extract the position of the first corneal surface 1412 and the second corneal surface 1414 (see also point 1516 in FIG. 15). Using the system 10 of FIGS. 1 and 2 to sample a first row scan (B-scan) along the scan range 1408, for example, the sample starting points 1422, 1424, 1426 appear in the output image 1420 as respective image points 1432, 1434, 1436. The respective image points 1432, 1434 and 1436 represent sample points of the first corneal surface 1412.

Referring to the output image 1430, the appearance of a bright or high intensity pixel, such as respective image points 1432, at a distance 1438 from the top edge of the output image 1430 may be converted to a three-dimensional location corresponding to the location of the sample starting point 1422 in the reference frame of the eye E. Each of the plurality of depth scans 1406 define respective starting points. The three-dimensional locations corresponding to the respective starting points of the plurality of depth scans 1406 may be similarly found, collected as a point cloud and converted to a single surface via a curve fitting technique. Referring to output image 1440 in FIG. 14B, the sample points 1444 may be fitted to a curve 1442.

As described previously, when the OCT module 14 and stereoscopic visualization camera 12 are registered, the three-dimensional position of a voxel in the respective data space of the OCT module 14 may be obtained. This allows the three-dimensional real-world position of each voxel to be obtained relative to a reference point on the stereoscopic visualization camera. A pixel's three-dimensional position is available as long as its three-dimensional location in the OCT data space is known, as it is by knowing, for example, its X and Y locations in the two-dimensional image as well as the index of the transverse slice that the image represents. Hence the location of each pixel in the output image 1420 may be converted to a real-world position in the reference frame of the stereoscopic visualization camera 12 and overlaid for display in the shared composite view.

When the first beam B1 of the OCT module 14 passes through a material to result in a detected surface point, the index of refraction of the material must be accounted for in that part of the light path during calculation of such distances. For example, light travels slower through plate glass than through the human cornea, so for two such structures of identical thickness, the resultant OCT data points reflecting off the front and rear surfaces of two such structures will be closer together for the cornea than for the plate glass. Accordingly, a refractive model generator available to those skilled in the art may be employed to generate a full or partial optical model of the patient's eye during surgery to enable assessment and subsequent improvement of optical aberrations present in the eye. The refractive model generator may employ the first set of volumetric data from the OCT module 14 such as the first volumetric sample 1452, second volumetric sample 1454 and third volumetric sample 1456 of the first corneal surface 1412, shown in FIG. 14B. The first volumetric sample 1452, second volumetric sample 1454 and third volumetric sample 1456 appear respectively in the output image 1460 as image points 1462, 1464, 1466. The refractive model generator may further employ the fourth volumetric sample 1472, fifth volumetric sample 1474 and sixth volumetric sample 1476 of the second corneal surface 1414, shown in FIG. 14B, which appear respectively in the output image 1460 as image points 1482, 1484, 1486. Additionally, the axial length 1560 of the eye E (see FIG. 15) may be employed.

Retinal Surgery: Visualization of Surface and Subsurface Features of the Retina

FIG. 15 is a schematic fragmentary sectional view showing the use of the system 10 to extract a 3D volumetric representation of an eye E having a lens 1416. At the portion 1530 of the retina, shown enlarged in FIG. 15, the higher-resolution, lower depth OCT configuration is used, with the nominal OCT working distance residing in or near the retina. Referring to FIG. 15, a plurality of depth scans 1502, 1504, 1506, 1508 or row scan 1532, are taken along the eye E. Referring to FIG. 15, the sampling point 1534 measures the front retinal surface 1510, while second sampling point 1536 images the rear retinal surface 1512 (see also point 1524). The subsurface sampling points 1538, 1540, 1542, 1544 image layers of the retina which here are showing a pathology 1550. The representation of the pathology 1550 is overlaid on the live view L such that the drawn pathology 1550 lines up with the pathology location in the live view L. This requires registration of the OCT module 14 and the stereoscopic visualization camera 12 as described above. The surgical team may locate pathologies and other objectives while viewing the eye E in the shared composite view, all on the same display. The surgical tools used are also visualized in the live image L. The pathology 1550 is not visible via a traditional microscope. The system 10 enables visualization of the pathology 1550 and hence more effective treatment. The integration, calibration and registration of the OCT module 14 and the stereoscopic visualization camera 12 enable greatly simplified location and guidance for the user.

Controlling Image Resolution and Range

Referring to FIG. 2, a user may select between a larger sample depth with a lower depth resolution and a smaller sample depth with higher depth resolution, via tradeoffs among the spectral width of the first light source 40 at the spot scan 60, the optical characteristics of the spot scan 60 and the resolution of the detector 44. For retinal surfaces, a depth scan with large sample depth with lower depth resolution may be employed. Referring to FIG. 15, such a depth scan passes through the pupil of the eye E, but also could potentially pass through the lens 1416, thereby sampling first and second lens points 1518 and 1520 on the lens 1416. Additionally, the vitreous humor 1526 may have some optical properties that are less than fully transparent. In some cases, due to surgical removal, the lens 1416 will not be present, similarly with the vitreous humor 1526, such that the determination of surface reflections is simplified somewhat. The spot scan 60 is movable about the target site 16 (see FIG. 2) using the steering unit 64 to within the limits of the OCT module 14. Additionally, the OCT range and resolution (e.g. low-depth/high resolution, etc.) are modifiable by switching among different optical setups in the OCT module 14 itself. This switching is fast, on the order of tens of milliseconds. With the integrated stereoscopic visualization camera 12 and OCT module 14 mounted on the robotic arm 24, the OCT sample volume may be moved about the target site 16 in a controlled fashion. This extends the OCT range significantly in the axial direction A and in the first and second transverse directions T1 and T2. The OCT readout and robot position may be recorded in such a way, for example, by including a universal timestamp of sufficient accuracy such that they may be later synchronized. From the registration process, the position and orientation of the target site 16 relative to a known reference on the stereoscopic visualization camera 12 are available, and the position and orientation of the reference are in turn known relative to the robot reference frame, the position and orientation of the target site 16 relative to the robotic arm may be obtained and controlled during an ophthalmic procedure employing such a range extension.

Measuring Axial Length of the Eye

Referring to FIG. 15, the system 10 may be employed to determine an axial length 1560 of the eye E, which is the distance from the first corneal surface 1412 to the front retinal surface 1510. Referring to FIG. 15, the axial length 1560 may be extracted by the difference in real-world coordinates between the measurement point 1514 on the first corneal surface 1412 and the measurement point 1522 on the front retinal surface 1510.

Axial length measurement of the patient's eye changes as a function of where the patient's eye is focused. In order to have a consistent measurement, the patient may be asked to focus on a fixed landmark built into the system 10. Alternatively or in addition, the axial length measurement may be taken continually during the surgery, for example by switching the OCT module 14 back and forth between its "low-depth, higher resolution" mode used to measure the first corneal surface 1412 and the second corneal surface 1414, and a "high-depth, lower resolution" which allows for measurement of the axial length 1560. By adjusting the steering unit 64 of FIG. 2, the spot scan 60 may be moved such that multiple measurements may be made to obtain an average value.

Extracting Curvature of the Cornea

Figure 16A:
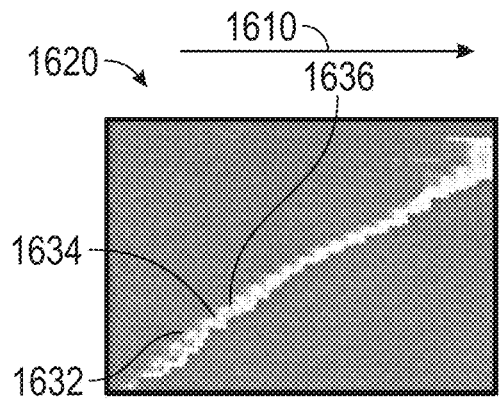
FIG. 16A is a schematic diagram of an output image of a single slice of the eye.
Figure 16B:
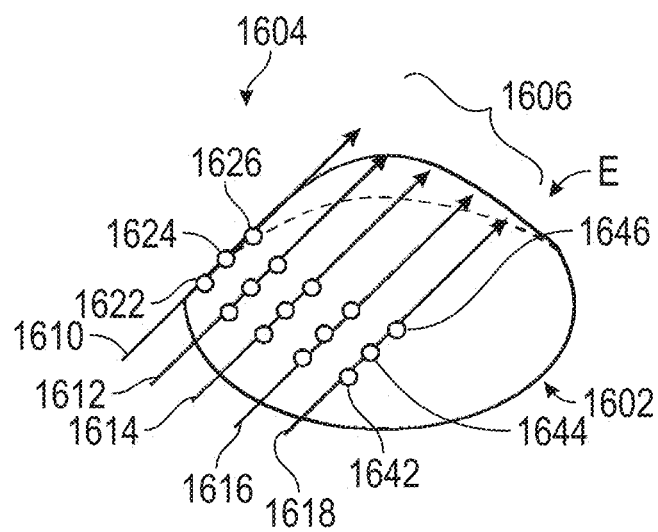
FIG. 16B is a schematic fragmentary perspective view of the eye, illustrating multiple slices across the surface of the eye.

Referring to FIG. 16B, the curvature of the front surface (or rear surface) of the cornea 1602 of the eye E may be obtained with the use of one or more row scans 1604 or slices covering the surface of the cornea 1602, such as first slice 1610, second slice 1612, third slice 1614, fourth slice 1616 and fifth slice 1618. FIG. 16A shows the output image of the first slice 1610. The cornea 1602 is transparent or semi-transparent at the wavelengths used in the first beam B1 and has a dimension that is less than the full depth range (see detected depth 204 in FIG. 4A) of the first beam B1. Thus a depth scan may be configured to encounter the cornea 1602 multiple times, with the sample path resulting in the detection of at least two reflection points along the path. For example, the first, second and third starting points 1622, 1624 and 1626 (of FIG. 16B) appear respectively in the output image 1620 of FIG. 16A as first, second and third image points 1632, 1634 and 1636.

Figure 16C:
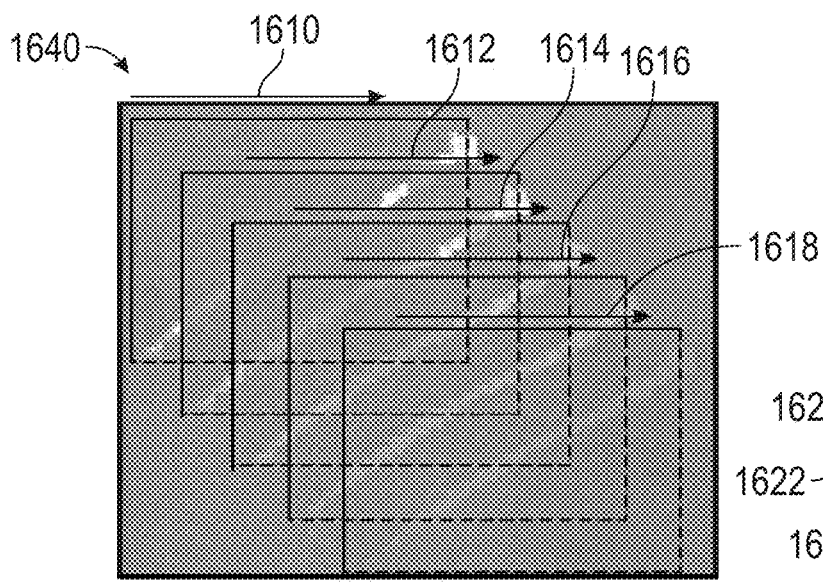
FIG. 16C is a schematic diagram of a superimposed image showing the outputs obtained from the multiple slices of FIG. 16B.

Referring to FIG. 16B, the row scans 1604 or slices may be extended or continued along a scan range 1606 to obtain or map further surface points. FIG. 16C shows a superimposed image 1640 of the respective outputs obtained from the first slice 1610, second slice 1612, third slice 1614, fourth slice 1616 and fifth slice 1618. To reduce noise in the image, noise reduction techniques may be employed. For example, thresholding on the intensity data may be performed by discarding outlying values below a low threshold and/or above a high threshold value. The outlying values may be set empirically using actual datasets.

Figure 16D:
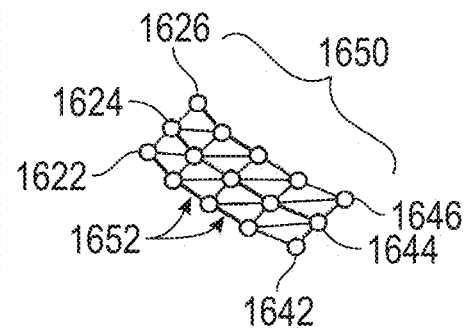
FIG. 16D is a schematic diagram showing the curvature of the cornea extracted through respective points on the multiple slices of FIG. 16B.

FIG. 16D is a schematic diagram showing a modeled or extracted surface 1650, obtained from the row scans 1604 of FIG. 16B. The controller C of FIG. 2 may be configured to first locate the reflection points in the first slice 1610, such as first, second and third starting points 1622, 1624 and 1626 in FIG. 16B. The reflection points in the (last) fifth slice 1618, such as fourth, fifth and sixth starting points 1642, 1644 and 1646 (see FIGS. 16B and 16D) are also obtained, as well as the respective starting points in the intermediate slices. For simplicity, only one surface of the cornea is shown in FIG. 16D. The collection of starting points may be fitted to a surface which matches prior assumptions. With enough detected points, a surface model 1652 is fitted to the points. The type or functional nature of the surface model 1652 may be varied. For simple curvature along a single B-scan direction of OCT data, a single two-dimensional slice of OCT is sufficient. To establish the maximum and minimum such curvatures, for example for the human cornea, multiple row scans 1604 may be used along the radial direction of the eye E. In such a manner, the curvature of both the first corneal surface 1412 and the second corneal surface 1414 (see FIG. 14B) along the scan range 1606 may be obtained, enabling estimation of the optical characteristics of the detected surfaces.

The curvature of the first corneal surface 1412 and the second corneal surface 1414 may change during the surgery due to incisions, removal of tissue, pressure changes and other reasons. Some of the changes may be intentional to offset or correct some existing irregularities in the eye. The surface curvature estimates may be done multiple times per second, providing the surgeon with up-to-date information as the surgery proceeds and as changes are made to the surfaces. This enables better patient outcomes as final incision results may be evaluated and adjusted. Using the faster "two B-scan" process described above also enables faster updates of this measurement when the scans are positioned along or nearly along the paths of such curvature on the eye and tracking is used to keep the scans so positioned.

By adjusting the steering unit 64 of FIG. 2, the spot scan 60 may be moved such that relevant portions of the desired structure are measured, for example, where there is sufficient curvature information. However, in human eye surgical scenes, the patient is typically awake and therefore the eye can move about the scene during the procedure. The optical center of the eye may found prior to the case, located with compensation due to cyclotorsion at the start of the case, and indicated with annotation over the live image L, such as for example on the shared composite view 300 of FIG. 5. While tracking various eye features in the live image L, the second annotation 330 may be kept in place onscreen relative to the eye E as the eye moves about naturally during the surgery. In some embodiments, the spot scan 60 may be moved with this tracking, keeping it located largely sampling the same volume of the eye E during the case. In other embodiments the OCT data itself is used to track the position of the eye by comparing frames near in time to each other and using a three-dimensional feature tracker to determine the amount of movement between frames. The "white-to-white" distance of the human eye is the horizontal diameter of the cornea. In some embodiments, the transverse range of the OCT module 14 may exceed this number, which enables the OCT sample volume when properly positioned to contain the cornea completely in the two transverse dimensions. Additionally, the range of radius of curvature of the cornea in humans results in an effective depth that is within the axial range of the OCT module 14. Thus, the OCT module 14 in some embodiments is able to sample the relevant regions of the full cornea including the whole front surface and rear surface.

The controller C may be configured to separately extract the first and second corneal surfaces 1412, 1414 (see FIG. 14) of the eye E captured by the OCT module 14 and generate a respective topographic map generated for each surface. The respective topographic map may be overlaid with the view from the 2D visualization modules V1, V2 of the stereoscopic visualization camera 12. Referring to FIG. 5, a live (stereoscopic) image L of the eye E is overlaid with a topographic outline 312, and shown on the first display 32. The shared composite view 300 of FIG. 5 may use different patterns to represent relative depth. The topographic outline 312 may be represented by a plurality of topographic levels, such as a first topographic level 314 and a second topographic level 316. The number of possible topographic levels is related to the axial resolution of the OCT module 14. The controller C may be configured to add at least one annotation 320 (dashed circle in FIG. 5) showing a boundary of the two-dimensional OCT view over the shared composite view 300. A second annotation 330 may indicate a landmark of the eye E. The controller C may be configured to maintain the relative position of the second annotation 330 on the first display 32 relative to other features of the eye E.

Astigmatism Correction: Extraction of Steep and Flat Axes of an Astigmatic Cornea Astigmatism in the human eye results partly from the cornea being shaped somewhat similar to an ellipsoid, with two marked curvature lines instead of a spherical shape with a uniform curvature across its surface. The system 10 may be employed to ascertain the degree of astigmatism in a patient, both as a diagnostic tool and during a corrective procedure in real time. In one example, referring to FIG. 17A, a plurality of depth scans 1702 of the cornea 1704 of an eye E are taken. The plurality of depth scans 1702 may be arranged in a star pattern 1706, with a plurality of row scans 1708 each crossing a center 1710, shown in FIG. 17A. While in the example shown in FIG. 17A, there are five row scans 1708, it is understood that any number may be employed. Additionally, other types of scan patterns may be employed.

Figure 17A:
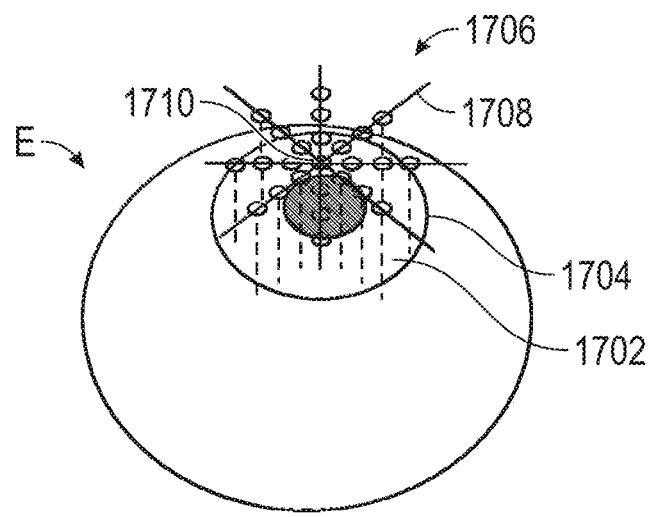
FIG. 17A is a schematic fragmentary perspective view of the eye, showing a plurality of depth scans arranged in a star pattern.
Figure 17B:
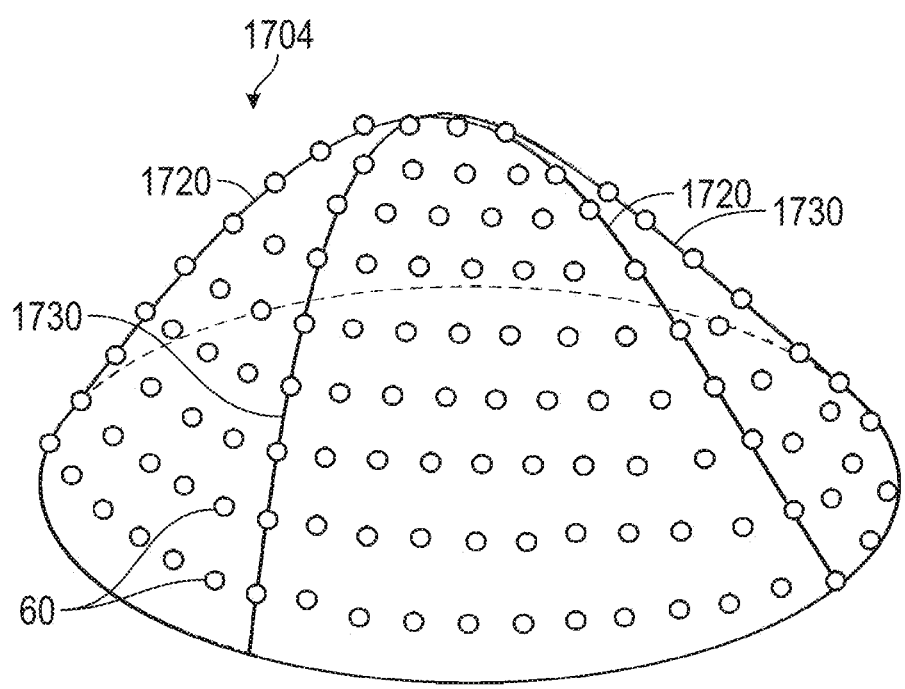
FIG. 17B is a schematic fragmentary perspective view of the eye, illustrating a steep axis and a flat axis of an astigmatic cornea, extracted through the plurality of depth scans of FIG. 17A.

FIG. 17B shows the cornea 1704 with multiple spot scans 60. Referring to FIG. 17B, the curvatures of interest extracted from the multiple spot scans 60 are a steep meridian 1720 and a flat meridian 1730, which are drawn as lines tracing the curvatures respectively, similar to lines of longitude on a globe. The steep meridian 1720 and the flat meridian 1730 may be found by tracking the maximum and minimum points of curvature on the cornea 1704. By using a star pattern 1706 shown in FIG. 17A, along with positioning the spot scan 60 approximately near the apex of the cornea 1704, each of the plurality of row scans 1708 will roughly transit these curvatures of interest, simplifying detection of the apex, the steep meridian 1720 and the flat meridian 1730. The steep meridian 1720 and the flat meridian 1730 may be drawn with different brightness, color/shades and/or patterns, for example, to allow the surgical team to differentiate from the background scene. Once an initial trace of the steep meridian 1720 and the flat meridian 1730 are made, the OCT module 14 may be placed into a faster "two B-scan" mode as described above, and the steep meridian 1720 and the flat meridian 1730 may be measured at a faster rate, allowing more real-time feedback and adjustments. This enables estimation of the extent of astigmatism of the eye E, enabling better selection and alignment of corrective lenses. The measurements with the system 10 may be made at time of surgery after some corrective incisions have been made, allowing for production of a fully custom lens tailored to this specific patient by, for example, 3D printing or otherwise manufacturing a lens while the patient is undergoing surgery.

Cataract Procedure: Adjustment of Intraocular Lens in Real-Time

Figure 18A:
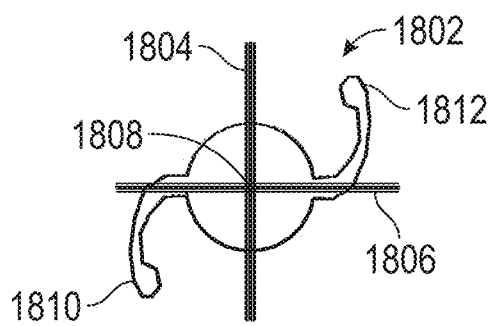
FIG. 18A is a schematic diagram of an intraocular lens configured for implantation into an eye.
Figure 18B:
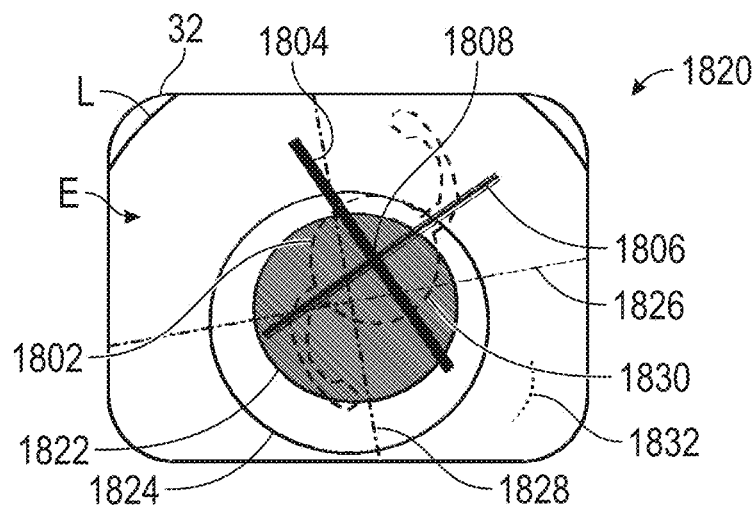
FIG. 18B is a schematic diagram of a shared composite view of an eye superimposed with the intraocular lens of FIG. 18A, the eye and the intraocular lens not being sufficiently aligned.

The system 10 may be employed for guiding an adjustment and subsequent implantation of an intraocular lens in real-time. FIG. 18A is a schematic diagram of an example intraocular lens 1802 configured for implantation into an eye, illustrated with a first lens axis 1804 and a second lens axis 1806, and centered at a lens origin 1808. The intraocular lens 1802 includes a first arm 1810 and a second arm 1812 for positioning the intraocular lens 1802. Referring to FIG. 18B, a first shared composite view 1820 of the eye E is shown on the first display 32 (or second display 34 of FIG. 1). FIG. 18B shows the pupil 1822 and the iris 1824. A first corneal axis 1826 and a second corneal axis 1828 and an eye center 1830 are drawn as overlays over the live image L, along with the intraocular lens 1802. In the first shared composite view 1820 of FIG. 18B, the first lens axis 1804 and the second lens axis 1806 are not sufficiently aligned with the first corneal axis 1826 and the second corneal axis 1828.

For an astigmatic patient undergoing a cataract procedure, the intraocular lens 1802 may be especially chosen to correct the astigmatism. For example, toric lenses are designed to be complimentary the patient's astigmatism, and must be aligned so that the complimentary (i.e. corrective) nature of the astigmatism correction is maximized. For best performance in both astigmatic as well as non-astigmatic patients, the intraocular lens 1802 is centered on the patient's visual axis so that the intraocular lens 1802 corrects the patient's vision as well as possible. To facilitate alignment of the first lens axis 1804 and the second lens axis 1806 with the first corneal axis 1826 and the second corneal axis 1828, surgeons may make physical markings on the eye to define a known axis to guide them during rotational adjustment of the intraocular lens. However, these markings may smudge and produce inaccuracies.

Figure 18C:
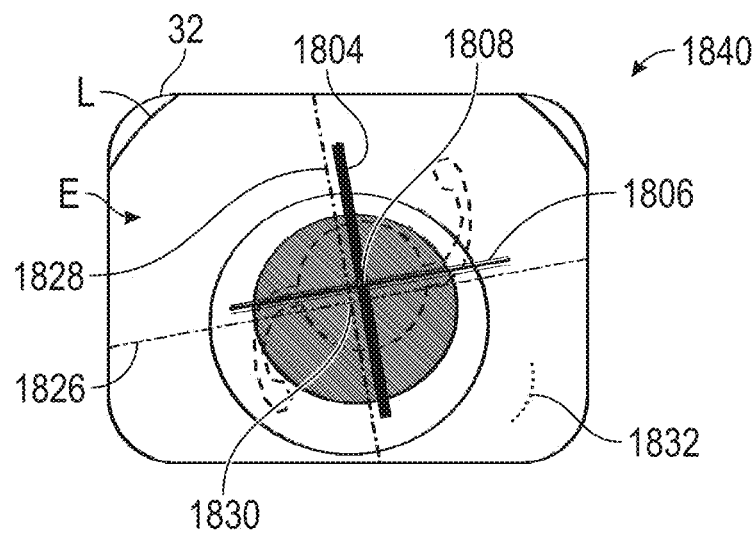
FIG. 18C is a schematic diagram of the shared composite view of FIG. 18B, with the curvature of the live surfaces extracted via the system being used to guide the placement of the intraocular lens and improve alignment.

FIG. 18C shows a second shared composite view 1840, using the curvature of the live surfaces extracted via the system 10 (as described above with respect to FIGS. 16A-D) to guide the placement of the intraocular lens 1802. Referring to FIGS. 18B and 18C, an annotated curvature 1832 may be drawn over or overlaid onto the live view L. The annotated curvature 1832 may be used by the surgeon to guide the movement of the intraocular lens 1802 and improve alignment.

The overlays may be updated with latency. As noted above, the stereoscopic visualization camera 12 and the OCT module 14 may define a respective latency. To mitigate this, the controller C may include a first set of image buffers configured to selectively delay the display of the two-dimensional OCT view in order to match the respective latency of the stereoscopic visualization camera 12. The controller C may include a second set of image buffers configured to do the opposite, and selectively delay the display of the two-dimensional stereoscopic view to match the respective latency of the OCT module 14. This enables the surgeon to align the first lens axis 1804 and the second lens axis 1806 with the first corneal axis 1826 and the second corneal axis 1828, thereby optimizing the implant procedure and resulting in better patient outcomes.

Alternatively, landmarks or features of the intraocular lens 1802 may be specified manually by a user, "locked in place" and tracked by the OCT module 14 and the stereoscopic visualization camera 12 during the ophthalmic procedure. The landmarks may include the lens origin 1808, and the respective location on the body of intraocular lens 1802 where the first arm 1810 and the second arm 1812 exit the body. The corneal shape may be changed during surgery, often intentionally. The intraoperative characterization of the corneal shape enabled by the system 10 also enables optimum specification of the intraocular lens 1802 to be implanted during a cataract procedure.

As noted above, intra-operative data obtained by the OCT module 14 may be employed to build a three dimensional model of the refractive surfaces during surgery. A refractive model generator algorithm available to those skilled in the art may be employed. By overlaying a reconstruction of this refractive model on top of the live view L, the surgeon may be able to assess the extent of astigmatism in real-time, thus helping to optimize the lens placement and orientation. Additionally, with the three dimensional model of the refractive surfaces being generated at the time of surgery, the parameters of the intraocular lens 1802 for implantation may be calculated more accurately than by other methods.

Corneal Transplants/Surgery: Visualization of Defects

A common cause of a poor outcome in corneal transplant procedures is a torn, folded, or wrinkled donor cornea placed inside the patient's eye. Because the cornea is optically transparent or semi-transparent, it may be extremely difficult to see these types of tears, folds or wrinkles. A surgeon may be able to see a tear, fold, or wrinkle with an OCT image, however, they will not necessarily know or be able to pinpoint the location of the abnormality when viewing the eye through a microscope.

Figure 19:
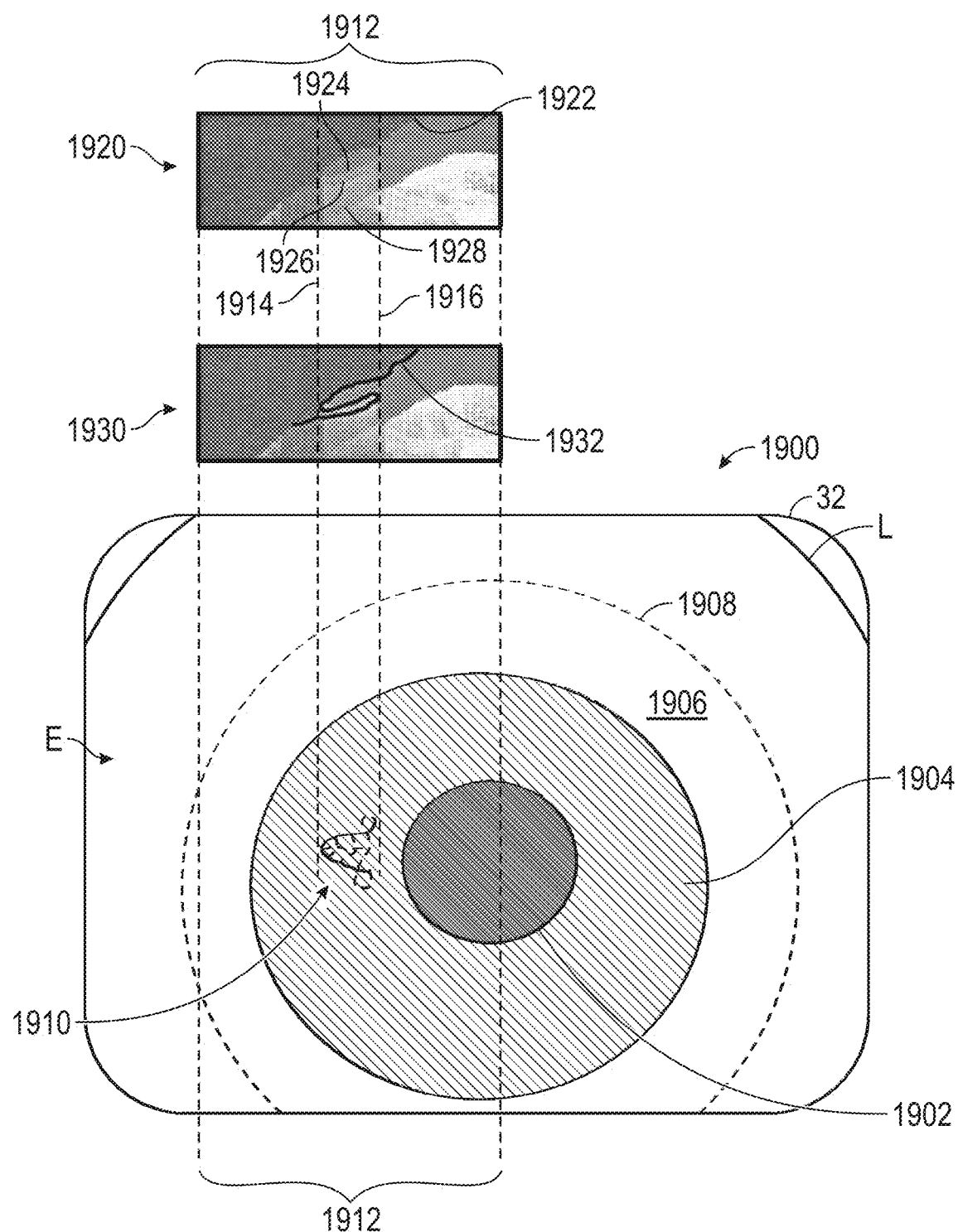
FIG. 19 is a schematic diagram of a shared composite view during a corneal procedure, showing visualization of a pathological region in the eye in real-time.

FIG. 19 illustrates visualization of a complication in a corneal procedure. Referring to FIG. 19, a schematic diagram of a shared composite view 1900 of an eye E, having a pupil 1902 and iris 1904, is shown. When the OCT module 14 and the 2D visualization modules V1, V2, of the stereoscopic visualization camera 12 are registered, the overlay (and fusing) of volume-rendered OCT data with the live view L onto the first display 32 (and/or second display 34), enables detection of and response to pathologies present in tissue that is difficult to visualize using traditional imaging modes.

During a corneal transplant the surgeon's goal is to remove by incision the patient's existing cornea (if present) and replace it with a donor cornea 1906 cut to approximately the same shape as the removed cornea. FIG. 19 illustrates the corneal transplant border 1908. As the cornea is a thin tissue, complications may arise during the transplant that are difficult to visualize. For example, referring to FIG. 19, the tissue may fold over itself, resulting in a pathological region 1910. The system 10 (see FIGS. 1 and 2) may detect multiple surfaces and layers simultaneously via a row scan 1912 (i.e. a B scan composed of a plurality of depth scans 202 as described above). The controller C may be configured to isolate the pathological region 1910 as being between a first border depth scan 1914 and a second border depth scan 1916., e.g. via the detection of multiple edges. The pathological region 1910 has multiple edges present in the fold which results in more "hits" for the first beam B1 (see FIG. 1) and a region of high pixel intensity. While the pathological region 1910 shown in FIG. 19 is a folded region, other pathologies such as tears, rips and wrinkles may be similarly isolated and visualized, enabling immediate detection and correction of such problems. For example, wrinkles have multiple surfaces while tears have discontinuities.

Referring to first output image 1920 from the row scan 1912 in FIG. 19, a top surface 1922 of the eye E may be imaged along with first portion 1924, second portion 1926 and third portion 1928. Referring to the second output image 1930 in FIG. 19, a curve 1932 may be fit along such surfaces. In this example, the controller C may be configured to display or annotate or draw in an overlay (solid line in FIG. 19) at the location of the pathological region 1910 for improved visualization. Additionally, the volume render process along with the registration method described above may enable drawing of a useful overlay without curve fitting. As more edges are present in a fold, this results in more "hits" for the first beam B1 and thus more "hits" for the cast virtual rays in the VR module 51. This enables a higher resultant value along those virtual rays for the pathological region 1910 compared to their surroundings, enabling the VR module 51 to differentiate visually these areas. The controller C may be configured to depict or visualize the pathological region 1910 with onscreen pixels of different brightness or color compared to the surroundings.

By employing a shared composite view as described above, and further highlighting or annotating the area where the pathological region 1910 is found, the surgeon may be shown precisely where they need to direct their attention. When combined with real-time OCT, this will further allow them to precisely manipulate the donor tissue to smooth out any folds or wrinkles, and to close together (as well as possible) any tears in the tissue. This method also works to enable or greatly improve the visibility of other difficult- or impossible-to-visualize tissue such as subsurface retinal lesions, tears, detachments and other pathologies.

Other Issues in Visualizing Eye Characteristics in Real-Time During Surgery

As noted above, latency overlays may be drawn over or intertwined appropriately with the live image L at a rate sufficient for the overlays to stay aligned in position and orientation to within an acceptable tolerance on moving objects to which they are meant to be aligned. There is a latency between the movement of the eye E and the update of the position and/or orientation and/or scale and/or perspective of the overlay meant for the eye E. This latency results in slight misalignment in such parameters, but reduces to the minimum tolerance for each parameter when the eye E stops moving (that is the overlay "catches up" to the object once the object stops moving). The latency is related to system speeds, such as imaging frame rates, display pipeline processing time etc. In some embodiments a set of image buffers are included in both imaging modality pipelines such that the latency of one modality relative to the other can be reduced or eliminated by delaying display of the other modality.

The system 10 enables tracking of various features of the eye E such as the viewing vector and the apex of the cornea. Such features are used to determine the "red reflex vector" which is the vector along which the second beam B2 from the stereoscopic visualization camera 12 is reflected from the patient's retina back into the stereoscopic visualization camera 12. Red reflex may be employed by surgeons to illuminate the patient's eye structures from within, for better diagnostics and improved procedure facilitation.

The controller C of FIG. 1 may be an integral portion of, or a separate module operatively connected to, other controllers integrated with the OCT module 14 and stereoscopic visualization camera 12. The controller C includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic media, a CD-ROM, DVD, other optical media, punch cards, paper tape, other physical media with patterns of holes, a RAM, a PROM, an EPROM, a FLASH-EEPROM, other memory chips or cartridges, or other media from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A method for guiding an ophthalmic procedure with a stereoscopic visualization camera and a controller with a processor and tangible, non-transitory memory on which instructions are recorded, the method comprising:

configuring a housing assembly with a head unit directed towards a target site in an eye;

obtaining a first set of volumetric data of the target site via an optical coherence tomography (OCT) module at least partially located in the head unit;

obtaining a second set of volumetric data of the target site, via the stereoscopic visualization camera at least partially located in the head unit, the second set of volumetric data including first and second views of the target site;
connecting a robotic arm to the head unit for selectively moving the head unit;
extending a viewing range of the OCT module in an axial direction, a first transverse direction and a second transverse direction, via selective movement of the head unit by the robotic arm;
registering the first set of volumetric data from the OCT module with the second set of volumetric data from the stereoscopic visualization camera to create a third set of registered volumetric data, via the controller;
rendering the third set of registered volumetric data to a first region to obtain a two-dimensional OCT view, via a volumetric render module selectively executable by the controller;
rendering the second set of volumetric data from the stereoscopic visualization camera to a second region to obtain a live two-dimensional stereoscopic view, via the volumetric render module, the stereoscopic visualization camera and the OCT module defining a respective latency; and
selectively delaying a display of the two-dimensional OCT view to match the respective latency of the stereoscopic visualization camera, via a first set of image buffers in the controller, and selectively delaying the display of the live two-dimensional stereoscopic view to match the respective latency of the OCT module, via a second set of image buffers.

2. The method of claim 1, further comprising:
overlaying the first region and the second region to obtain a shared composite view of the target site, via the controller.

3. The method of claim 1, further comprising, registering the first set of volumetric data from the OCT module with the second set of volumetric data by:
aligning the first and second views of the stereoscopic visualization camera respectively in rotation, translation and scale to the volumetric render module; and
matching respective perspectives of the first and second views of the stereoscopic visualization camera to the volumetric render module.

4. The method of claim 1, further comprising:
registering the first set of volumetric data with the second set of volumetric data by finding a respective location and respective orientation of a center of projection of a first two-dimensional visualization module and a second two-dimensional visualization module of the stereoscopic visualization camera relative to the respective location and the respective orientation of a respective data space of the OCT module.

5. The method of claim 1, further comprising:
registering the first set of volumetric data with the second set of volumetric data by aligning a local area of interest in the first set of volumetric data in position, orientation and size with the second set of volumetric data, the local area of interest including at least one of a corneal limbus and a scleral vasculature.

6. The method of claim 1, further comprising, prior to registering the first set of volumetric data with the second set of volumetric data:
calibrating the OCT module and calibrating the stereoscopic visualization camera, by placing a calibration device at the target site and fitting respective lines to respective surfaces of the calibration device in each of three orthogonal views.

7. The method of claim 1, further comprising:
obtaining a plurality of depth scans extending through a corneal surface, each of the plurality of depth scans defining respective starting points;
collecting respective three-dimensional locations corresponding to the respective starting points of the plurality of depth scans as a point cloud; and
converting the point cloud to obtain an extracted curvature, including interpolating between the respective starting points.

8. The method of claim 7, further comprising:
overlaying the first region and the second region to obtain a shared composite view of the target site, via the controller; and
visualizing the shared composite view with a plurality of topographic levels, via the controller, the extracted curvature being characterized by a plurality of depths, wherein the plurality of topographic levels respectively represent the plurality of depths such that the extracted curvature may be visualized.

9. The method of claim 8, further comprising:
adding at least one annotation over the shared composite view on a display, the at least one annotation indicating the extracted curvature, the ophthalmic procedure being a cataract surgery including implantation of an intraocular lens into an eye;
maintaining a relative position of the at least one annotation in the shared composite view; and
employing the extracted curvature to guide alignment of an intraocular device to the eye.

10. The method of claim 1, further comprising:
updating the first set of volumetric data at a first frequency and updating the second set of volumetric data at a second frequency.

11. The method of claim 1, further comprising:
obtaining respective axial length measurements in real time repeatedly during the ophthalmic procedure by switching the OCT module between a first resolution mode and a second resolution mode.

12. The method of claim 1, further comprising:
overlaying the first region and the second region to obtain a shared composite view of the target site, via the controller;
adding at least one annotation over the shared composite view on a display, the at least one annotation indicating a landmark of the eye; and
maintaining a relative position of the at least one annotation in the live two-dimensional stereoscopic view.

13. The method of claim 1, further comprising:
obtaining a plurality of row scans of a cornea, the ophthalmic procedure including astigmatism correction; and
extracting a steep meridian and a flat meridian from the plurality of row scans, via tracking of respective maximum and respective minimum points of curvature on the cornea.

14. The method of claim 13, further comprising:
arranging the plurality of row scans in a star pattern.

15. The method of claim 1, further comprising:
overlaying the first region and the second region to obtain a shared composite view of the target site, via the controller, and obtaining a plurality of depth scans of a cornea;
identifying and isolating a pathological region as being between a first one of the plurality of depth scans and a second one of the plurality of depth scans; and adding at least one annotation over the shared composite view on a display, the at least one annotation indicating the pathological region.

16. A system for imaging a target site, the system comprising:
a housing assembly having a head unit configured to be at least partially directed towards the target site;
an optical coherence tomography (OCT) module at least partially located in the head unit and operable to obtain a first set of volumetric data of the target site;
a stereoscopic visualization camera at least partially located in the head unit and configured to obtain a second set of volumetric data of the target site, the second set of volumetric data including first and second views of the target site;
a controller in communication with the stereoscopic visualization camera and the OCT module;
a volumetric render module selectively executable by the controller;
an oblique visualization module selectively executable by the controller to produce an off-axis view of a shared composite view such that a respective representation of the first set of volumetric data and the second set of volumetric data is viewed at a predefined oblique angle;
wherein execution of the oblique visualization module causes the controller to:
form a wireframe image based in part on the first set of volumetric data;
render the wireframe image as a first pair of stereo images;
render the second set of volumetric data as a second pair of stereo images; and
fuse the first pair of stereo images and the second pair of stereo images to form the off-axis view.

17. The system of claim 16, wherein the controller is adapted to:
register the first set of volumetric data from the OCT module with the second set of volumetric data from the stereoscopic visualization camera to create a third set of registered volumetric data;
render the third set of registered volumetric data to a first region to obtain a two-dimensional OCT view, via the volumetric render module;
render the second set of volumetric data from the stereoscopic visualization camera to a second region to obtain a live two-dimensional stereoscopic view, via the volumetric render module; and
overlay the first region and the second region to obtain the shared composite view of the target site.

18. The system of claim 17, wherein the predefined oblique angle is selectable by a user via a user interface.

19. A method for guiding an ophthalmic procedure with a stereoscopic visualization camera and a controller with a processor and tangible, non-transitory memory on which instructions are recorded, the method comprising:
configuring a housing assembly with a head unit directed towards a target site in an eye;
obtaining a first set of volumetric data of the target site via an optical coherence tomography (OCT) module at least partially located in the head unit;
obtaining a second set of volumetric data of the target site, via the stereoscopic visualization camera at least partially located in the head unit, the second set of volumetric data including first and second views of the target site;
calibrating the OCT module and calibrating the stereoscopic visualization camera, by placing a calibration device at the target site and fitting respective lines to respective surfaces of the calibration device in each of three orthogonal views;
registering the first set of volumetric data from the OCT module with the second set of volumetric data from the stereoscopic visualization camera to create a third set of registered volumetric data, via the controller;
rendering the third set of registered volumetric data to a first region to obtain a two-dimensional OCT view, via a volumetric render module selectively executable by the controller;
rendering the second set of volumetric data from the stereoscopic visualization camera to a second region to obtain a live two-dimensional stereoscopic view, via the volumetric render module, the stereoscopic visualization camera and the OCT module defining a respective latency; and
selectively delaying a display of the two-dimensional OCT view to match the respective latency of the stereoscopic visualization camera, via a first set of image buffers in the controller, and selectively delaying the display of the live two-dimensional stereoscopic view to match the respective latency of the OCT module, via a second set of image buffers.

* * * * *